United States Patent [19]

Junge et al.

[11] 4,229,343
[45] Oct. 21, 1980

[54] AZO DYES FROM AN OXADIAZOLYL-SUBSTITUTED ANILINE

[75] Inventors: Helmut Junge, Wachenheim; Walter Kurtz, Ludwigshafen; Peter Dimroth, Ludwigshafen; Hans Scherer, Ludwigshafen, all of Fed. Rep. of Germany

[73] Assignee: BASF Aktiengesellschaft, Fed. Rep. of Germany

[21] Appl. No.: 924,196

[22] Filed: Jul. 13, 1978

Related U.S. Application Data

[63] Continuation of Ser. No. 776,222, Mar. 10, 1977, abandoned, which is a continuation of Ser. No. 561,004, Mar. 21, 1975, abandoned.

[30] Foreign Application Priority Data

Apr. 9, 1974 [DE] Fed. Rep. of Germany ....... 2417217
Dec. 6, 1974 [DE] Fed. Rep. of Germany ....... 2457687

[51] Int. Cl.³ .............................................. C09B 29/18
[52] U.S. Cl. ................................... 260/156; 260/154; 260/155; 260/157; 260/162
[58] Field of Search ............... 260/157, 154, 155, 156, 260/162

[56] References Cited

U.S. PATENT DOCUMENTS

| | | | |
|---|---|---|---|
| 2,872,441 | 2/1959 | Kracker et al. ...................... | 260/157 |
| 3,923,777 | 12/1975 | Dimroth et al. .................... | 260/157 |

FOREIGN PATENT DOCUMENTS

| | | | |
|---|---|---|---|
| 929498 | 6/1955 | Fed. Rep. of Germany ........... | 260/157 |
| 2101558 | 7/1972 | Fed. Rep. of Germany ........... | 260/157 |
| 2417217 | 11/1975 | Fed. Rep. of Germany ........... | 260/157 |
| 2457687 | 6/1976 | Fed. Rep. of Germany ........... | 260/157 |

*Primary Examiner*—Arthur P. Demers
*Attorney, Agent, or Firm*—Keil & Witherspoon

[57] ABSTRACT

Compounds of the formula

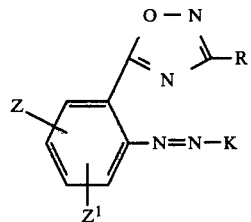

in which
K is

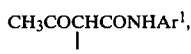

$CH_3COCHCONHAr^1$,

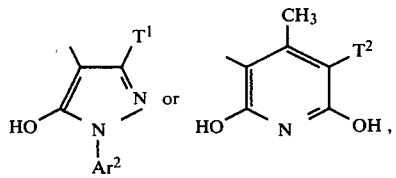

$Ar^1$ is phenyl; phenyl substituted by chlorine, methoxy, ethoxy, methyl, acetylamino or benzoylamino; or

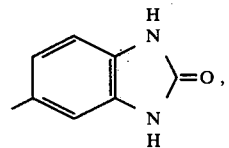

$Ar^2$ is phenyl; or phenyl substituted by chlorine, methyl or sulfamoyl,
$T^1$ is methyl or carbamoyl,
$T^2$ is cyano or carbamoyl,
Z is hydrogen, chlorine, bromine or trifluoromethyl,
$Z^1$ is hydrogen, chlorine, or bromine, and
R is phenyl; phenyl substituted by chlorine, bromine, hydroxy, methoxy, ethoxy, $C_1$ to $C_4$ alkyl, cyano, carbamoyl, nitro, phenyl, sulfamoyl, N-phenylsulfamoyl, acetylamino or benzoylamino; naphthyl; N-phenylphthalimidyl; or pyridyl.

These compounds are dyes having mostly pigmentary character and are eminently suitable for coloring printing inks, surface coatings and resins.///

5 Claims, No Drawings

AZO DYES FROM AN OXADIAZOLYL-SUBSTITUTED ANILINE

This application is a continuation of application Ser. No. 776,222 filed Mar. 10, 1977 and now abandoned, which in turn was a continuation of application Ser. No. 561,004 filed Mar. 21, 1975 and now abandoned.

This application discloses and claims subject matter described in German Patent Application No. P 24 17 217.6, filed Apr. 9, 1974 and German Patent Application No. P 24 57 687.2, filed Dec. 6, 1974, which are incorporated herein by reference.

The present invention relates to dyes of the general formula I

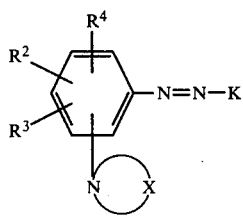

in which K is the radical of a coupling component, $R^3$ and $R^4$ independently of one another are hydrogen, chlorine, bromine, alkyl, alkoxy, nitro, cyano, alkylsulfonyl, arylsulfonyl, carboxyl, C-acylamino, carbamoyl, sulfamoyl, N-substituted carbamoyl or N-substituted sulfamoyl, carbalkoxy or quinazolonyl which may be substituted by chlorine, bromine or nitro, $R^2$ is hydrogen or

$CONHR^1$ or $SO_2NHR$, X is

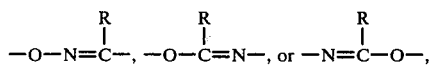

R is an optionally substituted aliphatic, cycloaliphatic, araliphatic, aromatic or heterocyclic radical and $R^1$ is hydrogen or a radical R, with the proviso that if

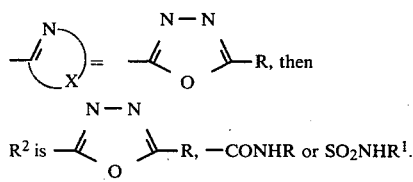

Specific examples of $R^3$ and $R^4$, in addition to those mentioned above, are methyl, ethyl, methoxy, ethoxy, acetylamino, propionylamino, benzoylamino, propionylamino, benzoylamino, methylsulfonyl, ethylsulfonyl, phenylsulfonyl, chlorophenylsulfonyl, N-phenyl-, N-chlorophenyl-, N-methylphenyl-, N-dichlorophenyl- or N-methoxyphenylcarbamoyl or N-methoxyphenylsulfamoyl, carbomethoxy and carboethoxy.

Preferably, $R^3$ and $R^4$ are hydrogen.

Examples of radicals R are alkyl of 1 to 8 carbon atoms, which may be substituted by hydroxyl, alkoxy of 1 to 4 carbon atoms, cyano, acyloxy, carbamoyl or N-substituted carbamoyl; cyclohexyl, benzyl, phenylethyl, styryl and phenyl; phenyl substituted by quinazolonyl, halogen, alkyl, alkoxy, alkylsulfonyl, cyano, nitro, carbamoyl, sulfamoyl, N-substituted carbamoyl or sulfamoyl, arylsulfonyl or acylamino; optionally N-substituted phthalimidyl, naphthyl, anthraquinonyl, pyridyl, 2,6-dihydroxypyridyl, quinazolonyl, quinolinyl, quinaldinyl and pyrimidinyl.

Specific examples of radicals R, in addition to those mentioned above, are: methyl, butyl, β-ethylhexyl, cyanomethyl, β-hydroxyethyl, β-ethoxyethyl, β-butoxyethyl, acetoxymethyl, carbamoylmethyl, N,N-dimethylcarbamoylmethyl, chlorophenyl, dichlorophenyl, methylphenyl, methoxyphenyl, methoxychlorophenyl, methoxydichlorophenyl, methylchlorophenyl, cyanophenyl, nitrophenyl, nitrochlorophenyl, nitromethoxyphenyl, nitromethylphenyl, sulfamoylphenyl, N-phenylsulfamoylphenyl, N-dichlorophenylsulfamoylphenyl, phenylsulfonylphenyl, acetylaminophenyl, benzoylaminophenyl, dichlorobenzoylaminophenyl and naphthoylaminophenyl as well as the radicals of the formulae

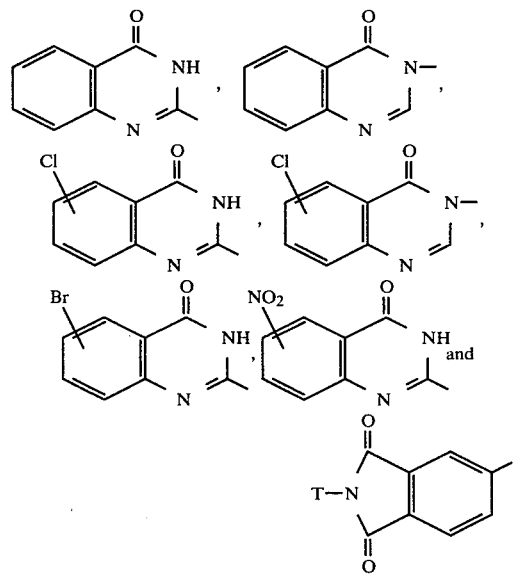

wherein T is hydrogen, methyl, ethyl, propyl, butyl, phenyl, chlorophenyl, dichlorophenyl, methylchlorophenyl, methoxyphenyl, dimethylphenyl or dimethylchlorophenyl. Within the compass of the general definition, examples of $R^1$ are the same as those mentioned for R.

Examples of coupling components are compounds of the phenol, naphthol, acetoacetarylide, pyrazolone, quinoline, pyridone, pyrimidone and isoquinolone series.

Examples of individual coupling components are: phenol, o-, m- or p-cresol, α-naphthol, β-naphthol, 2-naphthol-3-carboxylic acid esters and amides, such as acetoacetanilide, acetoacet-o-anisidide, 1-phenyl-3-methyl-pyrazolone, 1-phenyl-pyrazolone-3-carboxylic acid esters or amides, 2,4-dihydroxyquinoline, N-methyl-4-hydroxy-quinolone-2, 2,6-dihydroxy-3-cyano-4-methylpyridine, 2,6-dihydroxy-3-carbamoyl-4-methylpyridine, N-methyl-, N-γ-methoxypropyl-, N-butyl- or N-benzyl-2-hydroxy-3-cyano-4-methyl-pyridone-6, 2- amino-4,6-dihydroxypyrimidine, 2,4-dihydroxy-6-aminopyrimidine, 2,4-diamino-6-hydroxy-pyrimidine, 1,3-dimethyl-4-hydroxy-pyrimidine-2,6-dione and 1,3-dihydroxyisoquinoline.

The dyes of the formula I may be prepared by reacting a diazo compound of amines of the formula II

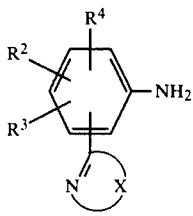

with a coupling component of the formula

HK . 

In the case of the manufacture of dyes with a 2-naphthol-3-carboxylic acid amide component, it can be advantageous to start from acid chlorides of the formula

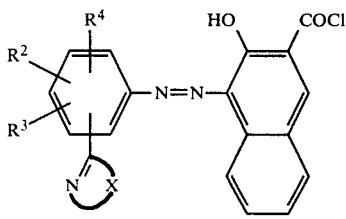

and convert these to the dye amides by reaction with the corresponding amines by conventional methods.

Dyes which may be used as pigments are in particular the compounds of the formula I wherein R is an aromatic radical and K is the radical of a coupling component of the β-naphthol, acetoacetarylide, pyrimidine, dihydroxyquinoline or dihydroxypyridine series. These dyes are highly insoluble in solvents and when used as pigments almost always exhibit good fastness to overcoating, to migration and to overspraying, and very good fastness to light. They can therefore be used, e.g., in printing inks, surface coatings or plastics such as PVC.

The pigments of the formula I are not always immediately obtained in the optimum physical form for particular end uses. However, they can be converted to the most suitable form by conventional methods such as grinding with salt, or heating in water or solvents.

The pigments of the invention may be used for pigmenting surface coatings and printing inks of all kinds, distempers and binder-based paints and for the mass coloring of synthetic, semisynthetic or natural macromolecular materials, e.g. polyvinyl chloride, polystyrene, polyamide or polyethylene. They may also be used for spin dyeing natural, regenerated or synthetic fibers, e.g. cellulose, polyester, polyacrylonitrile or nylon fibers. The pigments may be converted, by conventional methods, into pigment formulations, for example stable aqueous formulations for paints or for dyeing papers, or into nitrocellulose, PVC or other formulations which permit simple incorporation into the material to be colored.

The new dyes, especially those of the formula I a, have great tinctorial strength and brilliance and some of them have excellent fastness to light, very good fastness to overspraying, to solvents and to plasticizers, and good heat stability.

Other dyes of the formula I, in particular those wherein R is an aliphatic radical and the coupling component is a component of the cresol, N-alkylpyrimidine, N-alkylpyridine or N-alkylquinoline series, are good disperse dyes which may be used preferentially for dyeing polyester fibers and give dyeings of good fastness to light.

Dyes of the formula Ia

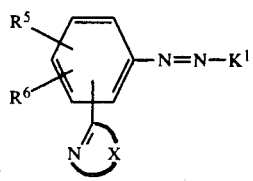

wherein $R^5$ is hydrogen, chlorine, bromine or nitro, $R^6$ is hydrogen or

and $K^1$ is the radical of a coupling component of the acetoacetarylide or pyrimidone series and especially of the pyridone or 2-naphthol-3-carboxylic acid arylamide series and X has the above meaning, are of particularly great industrial importance.

In particular, the invention relates to dyes of the formula

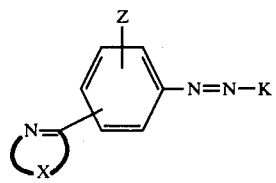

wherein K is

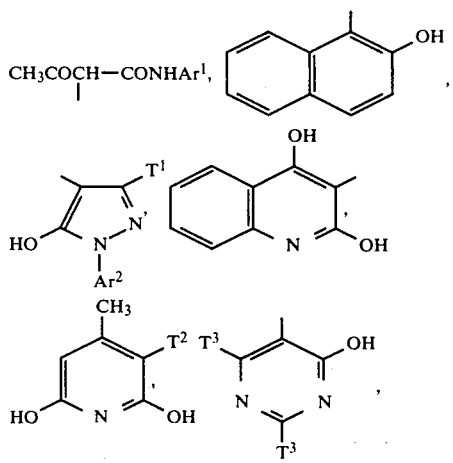

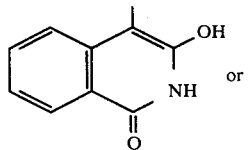

or

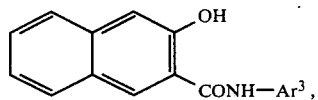

$Ar^1$ is phenyl or phenyl substituted by chlorine, methoxy, ethoxy, methyl, acetylamino or benzoylamino,

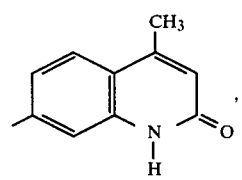

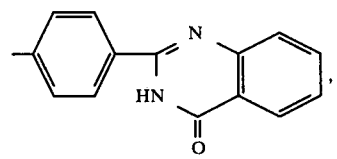

or

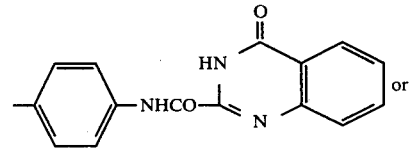

$Ar^2$ is phenyl or phenyl substituted by chlorine, methyl or sulfamoyl, $Ar^3$ is phenyl, phenyl substituted by chlorine, bromine, nitro, methoxy, ethoxy, alkyl of 1 to 4 carbon atoms, carbamoyl, sulfamoyl, N-phenylcarbamoyl, N-chloro-, N-methyl- or N-methoxy-phenylcarbamoyl, N-β-anthraquinonyl-carbamoyl, phthalimido, benzoylamino, benzoylamino substituted by chlorine, methyl, methoxy or acetylamino,

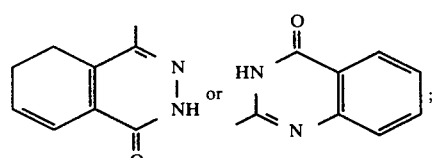

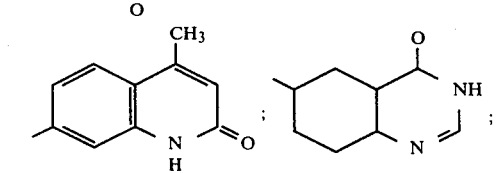

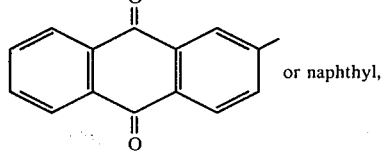 or naphthyl, $T^1$ is methyl or carbamoyl,
$R^2$ is cyano or carbamoyl,
$T^3$ is hydroxyl or amino,
X is

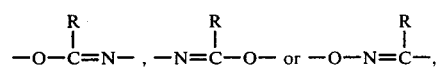

Z is

hydrogen, chlorine, bromine, methyl, ethyl, methoxy, ethoxy, nitro, cyano, methylsulfonyl, ethylsulfonyl, phenylsulfonyl, chlorophenylsulfonyl, alkoxycarbonyl of 1 to 4 carbon atoms, $CONHR^1$ or $SO_2NHR$, R is phenyl; phenyl substituted by chlorine, bromine, hydroxyl, methoxy, ethoxy, alkyl of 1 to 4 carbon atoms, cyano, carbamoyl, nitro, phenyl, sulfamoyl, N-phenylsulfamoyl, acetylamino, benzoylamino or benzoylamino substituted by chlorine, methyl, hydroxyl, methoxy or ethoxy; naphthyl, N-phenylphthalimidyl, anthraquinonyl, pyridyl or styryl, and $R^1$ is hydrogen; phenyl; phenyl substituted by chlorine, bromine, hydroxyl, methoxy, ethoxy, alkyl of 1 to 4 carbon atoms, cyano, carbamoyl, nitro, phenyl, sulfamoyl, N-phenylsulfamoyl, acetylamino, benzoylamino or benzoylamino substituted by chlorine, methyl, hydroxyl, methoxy or ethoxy; naphthyl, N-phenylphthalimidyl or anthraquinonyl, with the proviso that if

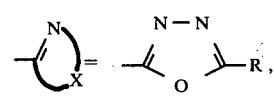

Z is

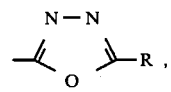

CONHR or $SO_2NHR^1$.

Preferred radicals R are optionally substituted phenyl or naphthyl, wherein the substituents may be, e.g., chlorine, bromine, methyl, methoxy, ethoxy, cyano, nitro or optionally N-substituted carbamoyl or sulfamoyl.

Further valuable compounds are those with quinazolonyl and optionally N-substituted phthalimidyl radicals. Because of the available methods of synthesis, the compounds containing the radical

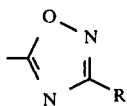

are preferred. Pigments with two

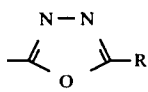

groups are also preferred.

In the preferred dyes, coupling components of the pyridone and pyrimidone series are free from substituents on the nitrogen atoms.

To manufacture the di-(1,3,4-oxdiazolyl)-anilines, the dichloride or dihydrazide of a dicarboxylic acid of the formula

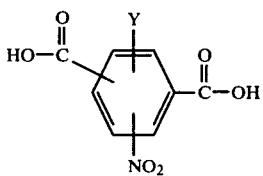

is reacted with carboxylic acid hydrazides or carboxylic acid chlorides of the formula

and the diacyl hydrazides thus obtained are treated with a reducing agent and a dehydrating agent.

Details of the manufacture of the compounds may be found in the Examples wherein parts and percentages are by weight, unless stated otherwise.

Sulfamoyl-2-[1,3,4-oxdiazolyl]-anilines are obtained by reacting isatoic anhydrides of the formula

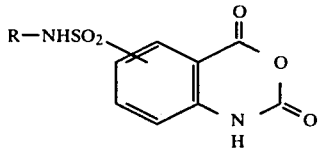

with carboxylic acid hydrazides of the formula

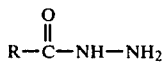

by conventional methods and then treating the products with dehydrating agents.

The sulfamoyl-substituted isatoic anhydrides may be obtained by reacting the corresponding ortho-halobenzoic acids (which are manufactured by, in part, conventional methods (U.P. Basu and S.J. De Gupta, J. Indian Chem. Soc. 16, 100 (1939)) first with ammonia and then with phosgene to give the corresponding isatoic anhydrides.

Corresponding carbamoyl-substituted 2-[1,3,4-oxdiazolyl]anilines are obtained analogously using correspondingly substituted anthranilic acids which have been manufactured analogously to the process of U.S. Pat. No. 2,808,433.

Synthesis of the other diazo components

Process A

31 Parts of sodium carbonate in 200 parts of water together with 55 parts of benzonitrile in 250 parts of isobutanol and 45 parts of hydroxylammonium sulfate are boiled under reflux for 4 hours. The aqueous phase is then separated off and 85 parts of isatoic anhydride are introduced in portions into the isobutanol phase at from 90° to 100° C. The mixture is stirred for a further 10 minutes and 4 parts of finely powdered sodium methylate are added at the boil, whereupon 2-(3-phenyl-1,2,4-oxdiazolyl)-aniline separates out as a thick paste of crystals. After cooling, the product is filtered off, rinsed with a little isobutanol and dried. Yield 110 parts. Melting point: 128°-130° C.

Process B 25 parts of nitroterephthalic acid dichloride are added to 28 parts of benzamidoxime in 40 parts of N-methyl-pyrrolidone at 25° C. and the mixture is then stirred for 2 hours at 160° C. and cooled to 100° C. 10 parts of water are added and the resulting paste of crystals is filtered off at 10° C., washed with methanol and dried at 100° C. This gives 330 parts of 2,5-bis-(3-phenyl-1,2,4-oxdiazolyl)nitrobenzene which are suspended in 2,000 parts of alcohol; a solution of 540 parts of sodium dithionite in 2,000 parts of water is added in the course of 1 hour to this suspension at from 60° to 70° C. The pH is kept at 6 by simultaneously adding 2 N NaOH solution. The mixture is stirred for a further hour at from 70° to 80° C. and the product is filtered off, washed thoroughly with water and dried at 100° C. Yield: 277 parts of 2,5-bis-(3-phenyl-1,2,4-oxdiazolyl)aniline (melting point: 249°-250° C.)

Process C 43.3 Parts of 2-nitroterephthalic acid dinitrile, 36 parts of sodium carbonate in 150 parts of water, 51 parts of hydroxylammonium sulfate and 200 parts of isobutanol are boiled for 2 hours under reflux, during which time the 2-nitroterephthalic acid bis-amidoxime separates out as crystals. These are filtered off, washed with water and dried. Yield: 43 parts. Melting point: 199°-200° C.

48 Parts of this product are dissolved in 80 parts of N-methylpyrrolidone and 56.2 parts of benzoyl chloride are added at room temperatue. The temperature is then raised to 160° C. in the course of 2 hours after which the mixture is cooled, 100 ml of methanol are added and the product is filtered off and dried. Yield: 48 parts of 2,5-bis-(5-phenyl-1,2,4-oxdiazolyl)-nitrobenzene. Melting point: 203° C.

41 Parts of this product in 250 parts of glacial acetic acid are boiled under reflux and 26 parts of zinc dust are added in portions. After 3 hours the mixture is diluted with 200 parts of water and filtered, the residue is dissolved in hot dimethylformamide, this solution is filtered and the product is precipitated with water, again filtered off and dried at 100° C. This gives 31 parts of 2,5-bis-(5-phenyl-1,2,4-oxdiazolyl)-aniline. Melting point 213°-125° C.

Process D

18 Parts of 2-nitrobenzamidoxime are suspended in 50 parts of nitrobenzene, 15.5 parts of benzoyl chloride are added and the mixture is heated to 160° C. for 3 hours. It is then concentrated under reduced pressure and the product is filtered off and washed with a little cold alcohol. Yield: 21 parts of 2-(5-phenyl-1,2,4-oxdiazolyl)-nitrobenzene.

19 Parts of this product, in 100 parts of alcohol, are reduced with a solution of 50 parts of sodium dithionite in 180 parts of water in the course of 30 minutes at 65° C. The pH is kept at 6 by simultaneously adding sodium hydroxide solution. The mixture is stirred for a further 30 minutes at 70° C. and the product is filtered off, washed with water and dried. Yield: 11 parts of 2-(5-phenyl-1,2,4-oxdiazolyl)-aniline. Melting point: 123°–124° C.

Process E

44 Parts of 3,4-dihydro-4-oxoquinazoline-2-carboxylic acid ethyl ester, 39 parts of 2-amino-5-nitro-benzamidoxime and 3 parts of p-toluenesulfonic acid in 200 parts of nitrobenzene are slowly heated to 160° C. and kept at this temperature for 2 hours. When the mixture is cold, the product is filtered, rinsed with methanol and dried. This gives 50 parts of a compound of the formula

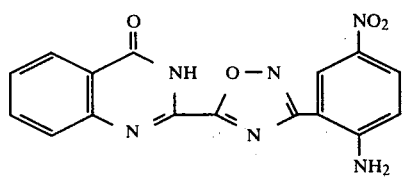

which melts, with decomposition, from 354° C. onward.

EXAMPLE 1

59.3 Parts of 2-(3-phenyl-1,2,4-oxdiazlyl)-aniline are added at from 10° to 15° C. to 250 parts of 98% strength sulfuric acid and are diazotized, after cooling to 0° C., by adding 80 parts of 45% strength nitrosylsulfuric acid. The mixture is stirred for 3 hours at 5° C. and, after destroying the excess nitrite by adding urea, is poured onto a mixture of 1,200 parts of ice and 600 parts of water; a solution of 37.5 parts of 3-cyano-2,6-dihydroxy-4-methyl-pyridine in 1.2 l of 0.5 N NaOH is added and the pH is brought to 4–5 with dilute sodium hydroxide solution. The batch is stirred for a further 5 hours and the product is filtered off and washed thoroughly with warm water. On drying, 93 parts of a brilliant yellow powder of the formula

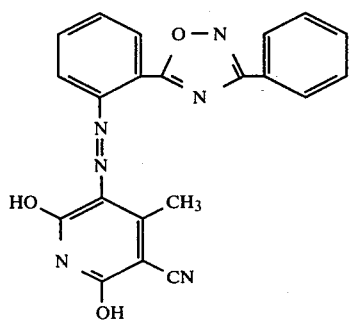

are obtained.

Dyes of the stated hue are obtained analogously to Example 1 from the diazo components shown in the table which follows. The individual diazo components are synthesized analogously to Instruction A.

| Ex. No. | Diazo component | Coupling component | Hue |
|---|---|---|---|
| 2 | ![diazo](o-N,=N,NH2 phenyl) | ![coupling](CH3, CONH2, HO-N-OH) | red |
| 3 | " | ![coupling](CH3, CN, HO-N=N-phenyl) | reddish orange |
| 4 | " | ![coupling](NH2, N, N, H2O, NH2) | yellow |
| 5 | " | ![coupling](OH, N, N, HO, OH) | yellow |

-continued
| Ex. No. | Diazo component | Coupling component | Hue |
|---|---|---|---|
| 6 | " | 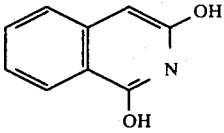 | yellow |
| 7 | " | CH₃—COCH₂—CONH—⟨⟩—NH—CO—CH₃ | yellow |
| 8 | " | 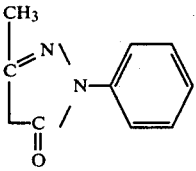 | yellow |
| 9 | " | 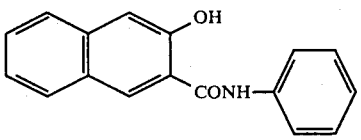 | yellow |
| 10 | " | CH₃—COCH₂—CONH—⟨⟩—NHCOCH₂—COCH₃ | yellow |
| 11 | " | 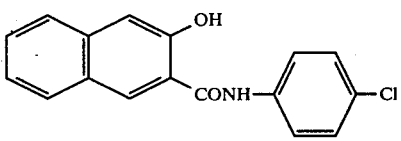 | red |
| 12 | " | 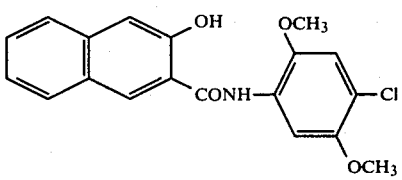 | red |
| 13 | " | 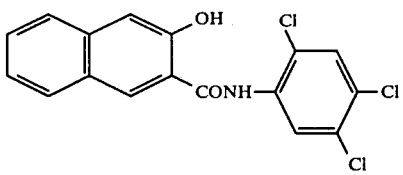 | red |
| 14 | " | 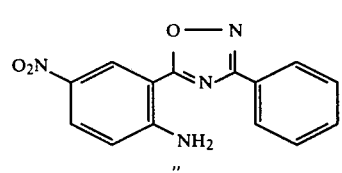 | red |
| 15 | 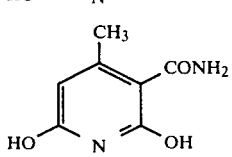 |  | yellow |
| 16 | " |  | yellow |

-continued

| Ex. No. | Diazo component | Coupling component | Hue |
|---|---|---|---|
| 17 | " | guanidine-derived pyrimidine with NH₂, N, N, H₂O, NH₂ groups | yellow |
| 18 | 5-nitro-2-amino phenyl with C=N-O-N=C-phenyl (oxadiazole-type) | isoquinoline-2,4-diol (OH, N, OH) | yellow |
| 19 | " | 4-methyl-pyrido-benzimidazole with HO, N, N | red |
| 20 | " | 2-hydroxy-pyrimidine-4,6-diol (OH, N, N, H₂O, OH) | yellow |
| 21 | " | $CH_3-COCH_2-CONH-\phi-NHCO-CH_3$ | yellow |
| 22 | " | $CH_3-COCH_2-CONH-\phi(NH-CO-NH)$ (benzimidazolone-acetoacetanilide) | yellow |
| 23 | " | $CH_3-COCH_2-CONH$-(4-methyl-2-oxo-quinolin-7-yl) | yellow |
| 24 | " | $CH_3-COCH_2-CONH-\phi-$(quinazolin-4(3H)-one-2-yl) | yellow |
| 25 | " | quinoline-2,4-diol | yellow |
| 26 | " | $CH_3-COCH_2-CONH-\phi-$phthalimide | yellow |
| 27 | 5-nitro-2-amino phenyl with 3-phenyl-1,2,4-oxadiazole | $H_3C-C(=N-N\phi)-CH_2-C(=O)$ (1-phenyl-3-methyl-5-pyrazolone type) | yellow |

| Ex. No. | Diazo component | Coupling component | Hue |
|---|---|---|---|
| 28 | " |  | yellow |
| 29 | " | 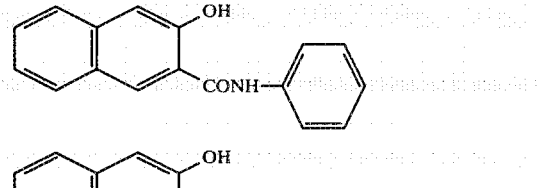 | red |
| 30 | " | 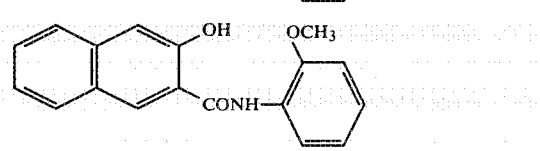 | red |
| 31 | " | 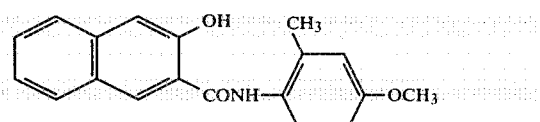 | red |
| 32 | " | 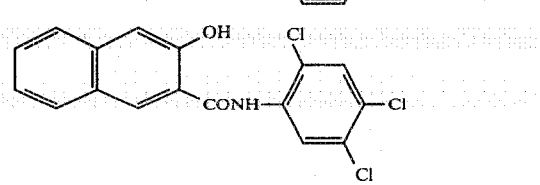 | red |
| 33 | " | 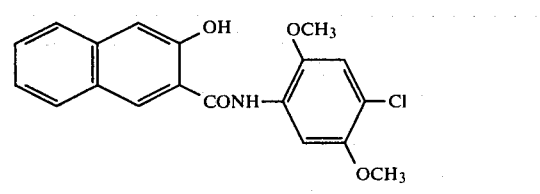 | brownish red |
| 34 | " | 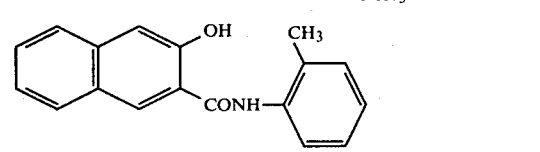 | red |
| 35 | " | 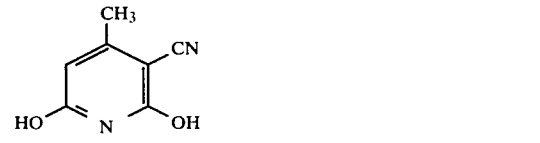 | red |
| 36 | 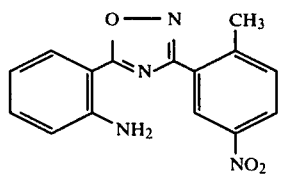 | 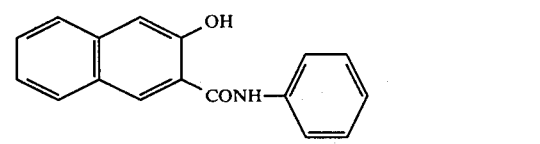 | yellow |
| 37 | " | 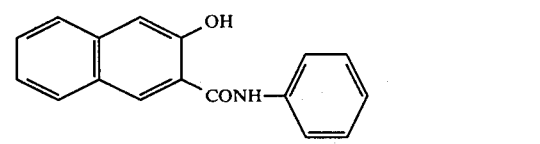 | red |
| 38 | " | 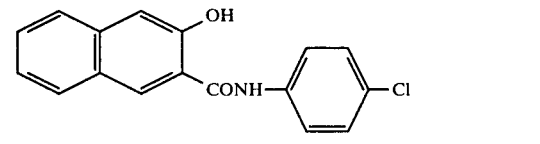 | red |

-continued
| Ex. No. | Diazo component | Coupling component | Hue |
|---|---|---|---|
| 39 | " | 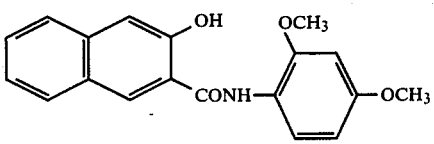 | red |
| 40 | 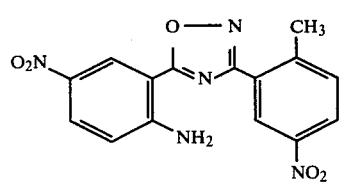 | 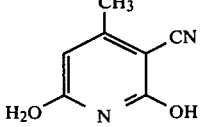 | yellow |
| 41 | " | 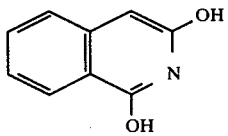 | yellow |
| 42 | " | 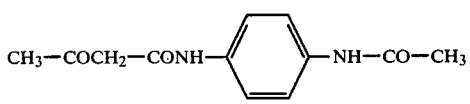 | yellow |
| 43 | " | 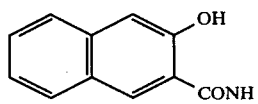 | red |
| 44 | " | 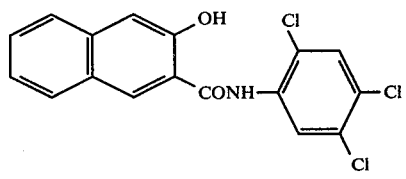 | red |
| 45 | 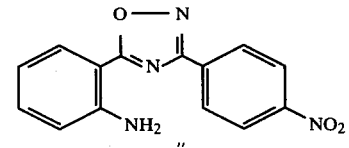 | 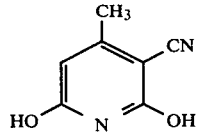 | yellow |
| 46 | " | 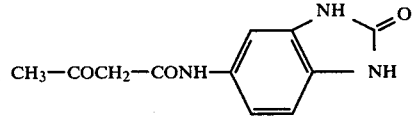 | yellow |
| 47 | " | 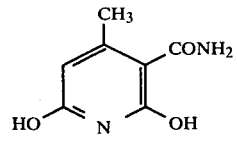 | yellow |
| 48 | " | 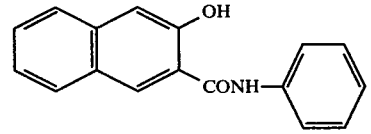 | red |
| 49 | " | 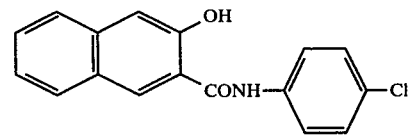 | red |
| 50 | " | 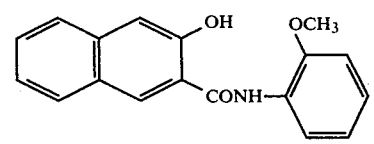 | red |

| Ex. No. | Diazo component | Coupling component | Hue |
|---|---|---|---|
| 51 | '' | 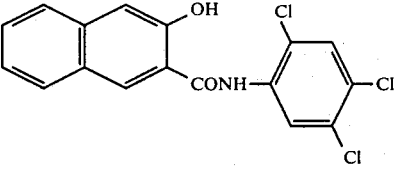 | red |
| 52 | 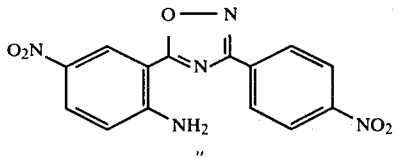 | 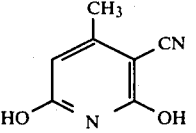 | yellow |
| 53 | '' | 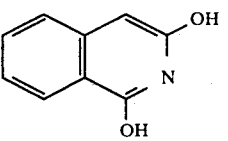 | yellow |
| 54 | '' | 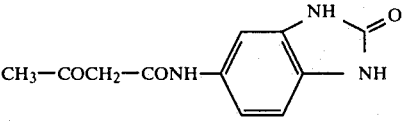 | yellow |
| 55 | '' | CH₃—COCH₂—CONH—⬡—NH—CO—CH₃ | yellow |
| 56 | '' | 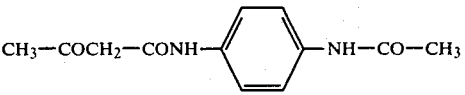 | red |
| 57 | '' | 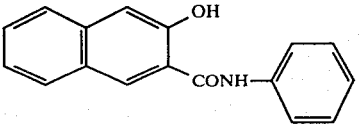 | red |
| 58 | '' | 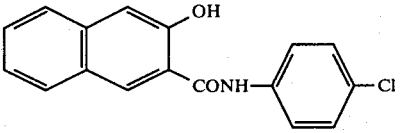 | brownish red |
| 59 | '' | 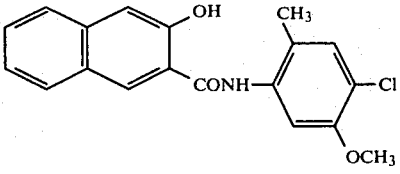 | red |
| 60 | '' | 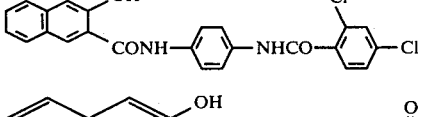 | red |
| 61 | 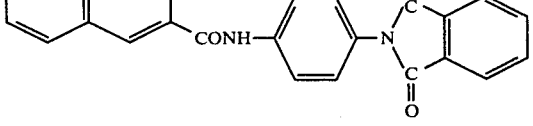 | 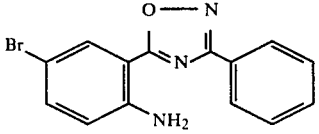 | yellow |

-continued

| Ex. No. | Diazo component | Coupling component | Hue |
|---|---|---|---|
| 62 | " | CH₃—COCH₂—CONH—(phenyl with NH-CO-NH urea group) | yellow |
| 63 | " | 3-hydroxy-2-naphthoyl-(4-chloroanilide) | red |
| 64 | " | 3-hydroxy-2-naphthoyl-NH—C₆H₄—NHCO—(2,5-dichlorophenyl) | red |
| 65 | 2-amino-4-chloro-(3-phenyl-1,2,4-oxadiazol-5-yl)benzene | 3-cyano-4-methyl-2,6-dihydroxypyridine | yellow |
| 66 | " | isoindoline/phthalimide-type (OH, N, OH) | yellow |
| 67 | " | 3-hydroxy-2-naphthoyl-(4-chloroanilide) | red |
| 68 | " | 3-hydroxy-2-naphthoyl-(2,4,5-trichloroanilide) | red |
| 69 | " | 3-hydroxy-2-naphthoyl-NH—C₆H₄—CONH—(3-chloro-4-methoxyphenyl) | red |
| 70 | 2-amino-4-chloro-[3-(4-chlorophenyl)-1,2,4-oxadiazol-5-yl]benzene | 3-cyano-4-methyl-2,6-dihydroxypyridine | yellow |
| 71 | " | 3-hydroxy-2-naphthoyl-(4-chloroanilide) | red |
| 72 | 2-amino-4-chloro-[3-(4-nitrophenyl)-1,2,4-oxadiazol-5-yl]benzene | 3-cyano-4-methyl-2,6-dihydroxypyridine | yellow |
| 73 | " | CH₃—COCH₂—CONH—(phenyl with NH-CO-NH urea group) | yellow |

-continued
| Ex. No. | Diazo component | Coupling component | Hue |
|---|---|---|---|
| 74 | 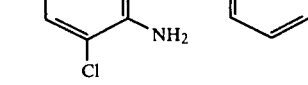 | 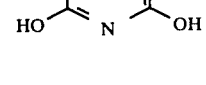 | yellow |
| 75 | " | CH₃—COCH₂—CONH—⟨⟩—NHCO—CH₃ | yellow |
| 76 | " | 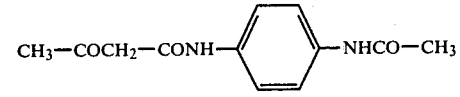 | red |
| 77 | " | 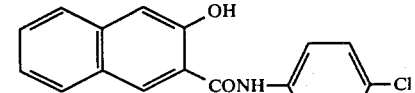 | red |
| 78 | " | 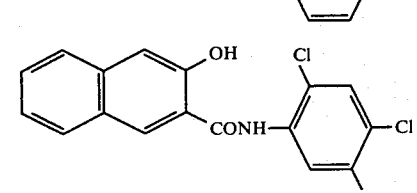 | red |
| 79 | 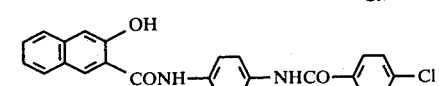 | 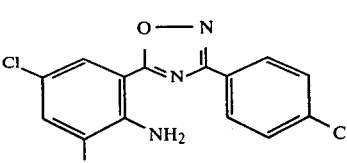 | yellow |
| 80 | " | 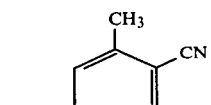 | red |
| 81 | 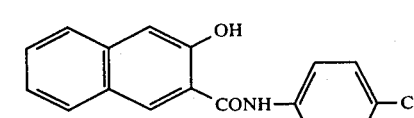 | 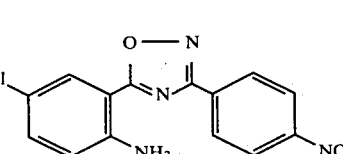 | red |
| 82 | 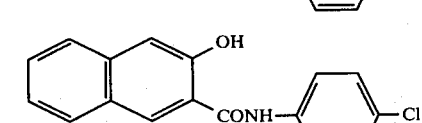 | 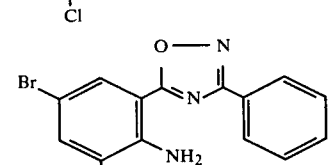 | yellow |
| 83 | " | 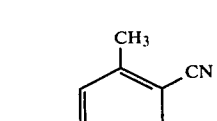 | yellow |
| 84 | " | CH₃—COCH₂—CONH—⟨⟩—NHCO—CH₃ | yellow |

| Ex. No. | Diazo component | Coupling component | Hue |
|---|---|---|---|
| 85 | " | 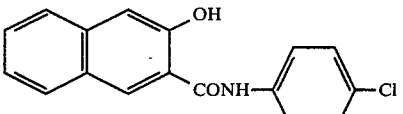 | red |
| 86 | " | 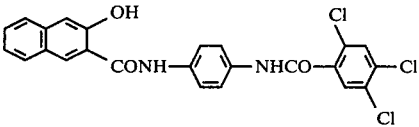 | red |
| 87 | 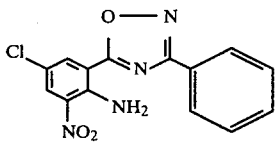 | 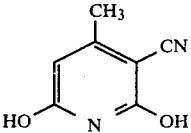 | yellow |
| 88 | " | 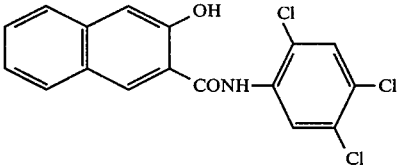 | red |
| 89 | 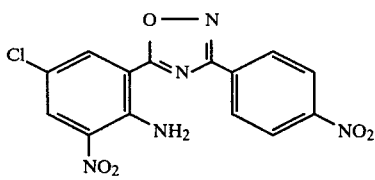 | 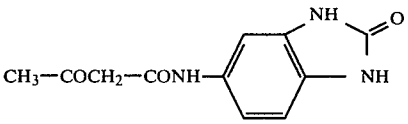 | yellow |
| 90 | " | 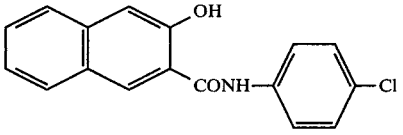 | red |
| 91 | 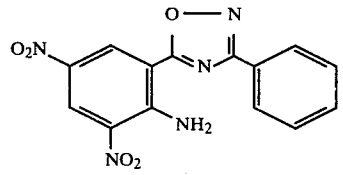 | 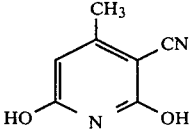 | yellow |
| 92 | " | 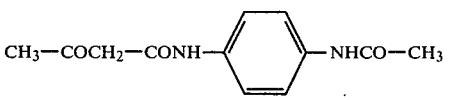 | yellow |
| 93 | " | 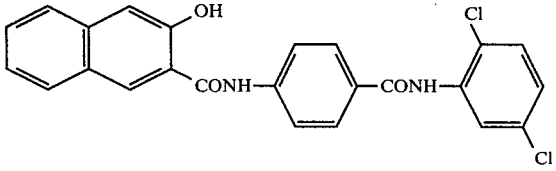 | red |
| 94 | " | 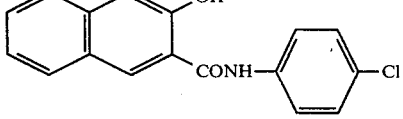 | red |

-continued

| Ex. No. | Diazo component | Coupling component | Hue |
|---|---|---|---|
| 95 | 2-amino-3,5-dinitrophenyl / 4-nitrophenyl 1,2,4-oxadiazole | 4-methyl-3-cyano-2,6-dihydroxypyridine | yellow |
| 96 | " | 3-hydroxy-2-naphth-(4-chloro-2,5-dimethoxyanilide) | red |
| 97 | 2-amino-4-nitrophenyl / phenyl 1,2,4-oxadiazole | 4-methyl-3-cyano-2,6-dihydroxypyridine | yellow |
| 98 | " | $CH_3-COCH_2-CONH-$ (benzimidazolone) | yellow |
| 99 | " | (isoindolinone/hydroxy structure) | yellow |
| 100 | " | acetoacetanilide imine | yellow |
| 101 | " | 3-hydroxy-2-naphth-(4-chloroanilide) | red |
| 102 | " | 3-hydroxy-2-naphth-(2-methylanilide) | red |
| 103 | " | 3-hydroxy-2-naphth-(2-methoxyanilide) | red |
| 104 | 2-amino-4-nitrophenyl / 4-chlorophenyl 1,2,4-oxadiazole | 4-methyl-3-cyano-2,6-dihydroxypyridine | yellow |
| 105 | " | $CH_3-COCH_2-CONH-\text{C}_6\text{H}_4-NHCO-CH_3$ | yellow |

-continued

| Ex. No. | Diazo component | Coupling component | Hue |
|---|---|---|---|
| 106 | 2-amino-4-nitrophenyl-(4-chlorophenyl)-1,2,4-oxadiazole | 3-hydroxy-N-phenyl-2-naphthamide | red |
| 107 | " | 3-hydroxy-N-(4-chlorophenyl)-2-naphthamide | red |
| 108 | 2-amino-4-nitrophenyl-(4-nitrophenyl)-1,2,4-oxadiazole | 3-cyano-4-methyl-2,6-dihydroxypyridine | yellow |
| 109 | " | CH₃—COCH₂—CONH—(phenylene with NHC(O)NH)— | yellow |
| 110 | " | 3-hydroxy-N-phenyl-2-naphthamide | red |
| 111 | " | 3-hydroxy-2-naphthoyl-amino-benzanilide | red |
| 112 | " | 3-hydroxy-N-(4-chlorophenyl)-2-naphthamide | red |
| 113 | 2-amino-4-trifluoromethylphenyl-phenyl-1,2,4-oxadiazole | 3-cyano-4-methyl-2,6-dihydroxypyridine | yellow |
| 114 | " | CH₃—COCH₂—CONH—(phenylene)—NHCOCH₂—COCH₃ | yellow |
| 115 | " | 3-hydroxy-N-(4-chlorophenyl)-2-naphthamide | red |
| 116 | 2-amino-4-trifluoromethylphenyl-phenyl-1,2,4-oxadiazole | 3-hydroxy-N-(2,4,5-trichlorophenyl)-2-naphthamide | red |

-continued

| Ex. No. | Diazo component | Coupling component | Hue |
|---|---|---|---|
| 117 | " | 3-hydroxy-N-(2-methoxyphenyl)-2-naphthamide | red |
| 118 | " | 3-hydroxy-N-[3-chloro-4-(2,4-dichlorobenzamido)phenyl]-2-naphthamide | red |
| 119 | 2-amino-4-(trifluoromethyl)phenyl / 4-nitrophenyl-1,2,4-oxadiazole (o-amino / CF₃ on one ring, NO₂ on other) | 3-cyano-2,6-dihydroxy-4-methylpyridine | yellow |
| 120 | " | CH₃—COCH₂—CONH—[2-ureidophenyl] | yellow |
| 121 | " | 3-hydroxy-N-(2-methoxyphenyl)-2-naphthamide | red |
| 122 | 2-amino-phenyl / 1-naphthyl-1,2,4-oxadiazole | 3-cyano-2,6-dihydroxy-4-methylpyridine | yellow |
| 123 | " | 3-hydroxy-N-(2-methylphenyl)-2-naphthamide | red |
| 124 | " | 3-hydroxy-N-(2,5-dimethoxy-4-chlorophenyl)-2-naphthamide | red |
| 125 | 2-amino-5-nitrophenyl / 1-naphthyl-1,2,4-oxadiazole | CH₃—COCH₂—CONH—C₆H₅ | yellow |
| 126 | " | 3-hydroxy-N-(4-chlorophenyl)-2-naphthamide | red |
| 127 | " | 3-hydroxy-N-(2-methoxyphenyl)-2-naphthamide | red |

-continued
| Ex. No. | Diazo component | Coupling component | Hue |
|---|---|---|---|
| 128 | " | 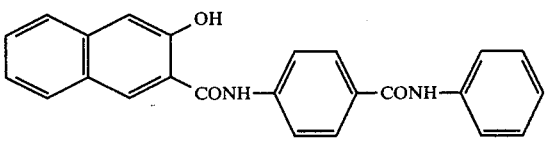 | red |
| 129 | 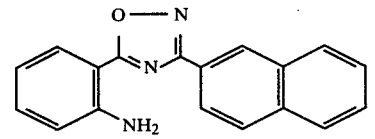 | 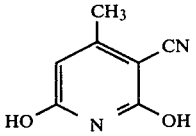 | yellow |
| 130 | " | 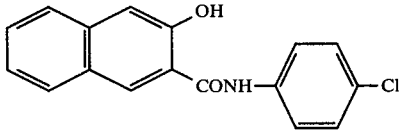 | red |
| 131 | " | 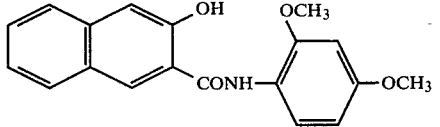 | red |
| 132 | 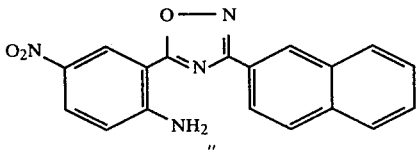 | CH₃—COCH₂—CONH—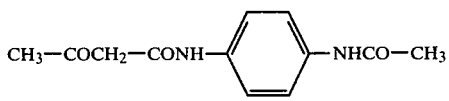—NHCO—CH₃ | yellow |
| 133 | " | 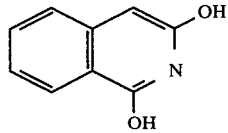 | yellow |
| 134 | " | 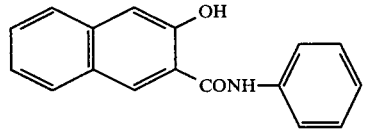 | red |
| 135 | " | 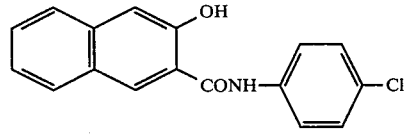 | red |
| 136 | " | 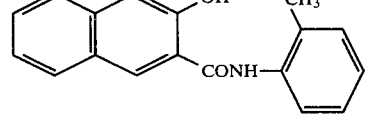 | red |
| 137 | " | 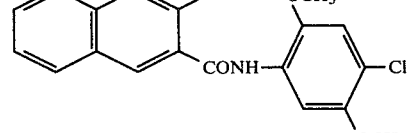 | red |
| 138 | 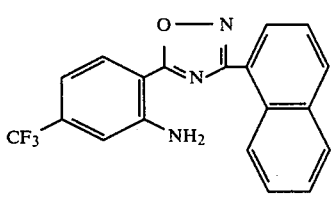 | CH₃—COCH₂—CONH—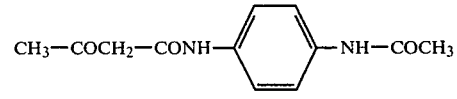—NH—COCH₃ | yellow |

-continued

| Ex. No. | Diazo component | Coupling component | Hue |
|---|---|---|---|
| 139 | " | 3-hydroxy-2-naphthoic acid anilide | red |
| 140 | " | 3-hydroxy-2-naphthoic acid 4-chloroanilide | red |
| 141 | " | 3-hydroxy-2-naphthoic acid 2,4,5-trichloroanilide | red |
| 142 | 2-amino-phenyl / 4-chlorophenyl 1,2,4-oxadiazole | 3-cyano-4-methyl-2,6-dihydroxypyridine | yellow |
| 143 | 2-amino-phenyl / 4-chlorophenyl 1,2,4-oxadiazole | HO-CH=CH-C(NH₂)=N-C(NH₂)=N (guanidine derivative) | yellow |
| 144 | " | 3-hydroxy-2-naphthoic acid chloroanilide | red |
| 145 | 2-amino-5-nitrophenyl / 4-chlorophenyl 1,2,4-oxadiazole | 3-cyano-4-methyl-2,6-dihydroxypyridine | yellow |
| 146 | " | 3-hydroxy-2-naphthoic acid 4-chloroanilide | red |
| 147 | " | 3-hydroxy-2-naphthoic acid 2-methoxyanilide | red |
| 148 | 2-amino-4-trifluoromethylphenyl / 2-naphthyl 1,2,4-oxadiazole | CH₃—COCH₂—CONH—C₆H₄—COCH₃ | yellow |
| 149 | " | 3-hydroxy-2-naphthoic acid 4-chloroanilide | red |

| Ex. No. | Diazo component | Coupling component | Hue |
|---|---|---|---|
| 150 | " | 3-hydroxy-N-(2-methoxyphenyl)-2-naphthamide | red |
| 151 | " | 3-hydroxy-N-(2,4,5-trichlorophenyl)-2-naphthamide | red |
| 152 | 2-amino-4-nitrophenyl 1-naphthyl 1,2,4-oxadiazole | 3-cyano-2,6-dihydroxy-4-methylpyridine | yellow |
| 153 | " | CH₃—COCH₂—CONH—C₆H₃(NH—CO—NH—) | yellow |
| 154 | " | 3-hydroxy-N-phenyl-2-naphthamide | red |
| 155 | " | 3-hydroxy-N-(4-chlorophenyl)-2-naphthamide | red |
| 156 | 2-amino-4-nitrophenyl 2-naphthyl 1,2,4-oxadiazole | CH₃—COCH₂—CONH—C₆H₄—NHCO—CH₃ | yellow |
| 157 | " | 3-hydroxy-N-phenyl-2-naphthamide | red |
| 158 | " | 3-hydroxy-N-(2-methoxyphenyl)-2-naphthamide | red |
| 159 | 2-aminophenyl 3-pyridyl 1,2,4-oxadiazole | 3-cyano-2,6-dihydroxy-4-methylpyridine | yellow |
| 160 | " | 3-hydroxy-N-(4-chlorophenyl)-2-naphthamide | red |

| Ex. No. | Diazo component | Coupling component | Hue |
|---|---|---|---|
| 161 | ![structure with O-N oxadiazole, O2N, NH2, pyridyl] | ![2-naphthol OH, CONH-phenyl(Cl)-NHCO-phenyl(Cl,Cl)] | red |

EXAMPLE 162

19.1 Parts of 2,5-bis-(3-phenyl-1,2,4-oxdiazolyl)-aniline are introduced into a mixture of 100 parts of glacial acetic acid and 100 parts of propionic acid and diazotized at 0°–5° C. by adding 15 parts of 45% strength nitrosylsulfuric acid. The mixture is stirred for a further 4 hours at 5° C. and a solution of 13.2 parts of 2-naphthol-3-carboxylic acid N-phenylamide in 150 parts of dimethylformamide is then added, followed by 70 parts of pyridine added slowly. The mixture is stirred for a further 6 hours at room temperature and then for 2 hours at 80° C. and the product is filtered off, washed thoroughly with water and methanol and dried at 80° C. This gives 25 parts of a reddish orange powder of the formula

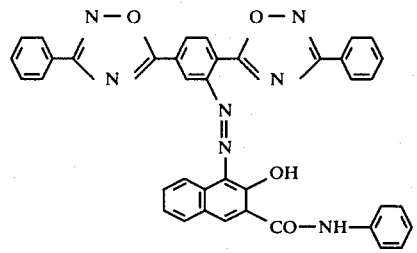

EXAMPLES 163–251

The procedure described in Example 162 is followed, using the diazo components and coupling components shown in the table. The individual diazo components are manufactured according to Instructions A to E, as shown alongside the diazo component in the table.

| Ex. No. | Diazo component | Coupling component | Hue |
|---|---|---|---|
| 163 | ![bis-oxadiazolyl aniline with NH2, B] | ![CH3, CN, HO, N, OH pyridone-type] | yellow |
| 164 | " | ![2-naphthol-CONH-phenyl-Cl] | reddish orange |
| 165 | ![CH3O-phenyl-bis-oxadiazolyl-phenyl-OCH3 B] | ![2-naphthol-CONH-phenyl(OCH3,Cl,OCH3)] | reddish orange |
| 166 | ![Cl-phenyl-bis-oxadiazolyl-phenyl-Cl with NH2, B] | ![CH3COCH2CONH-phenyl-NH-CO-CH3] | yellow |
| 167 | " | ![2-naphthol-CONH-phenyl-Cl] | reddish orange |
| 168 | ![naphthyl-bis-oxadiazolyl-phenyl-naphthyl with NH2, B] | ![2-naphthol-CONH-phenyl-Cl] | red |
| 169 | " | ![2-naphthol-CONH-phenyl(Cl,Cl,Cl)] | red |

-continued

| Ex. No. | Diazo component | Coupling component | Hue |
|---|---|---|---|
| 170 | (naphthyl-C(=N-O-)—phenyl(NH2)—C(=N-O-)naphthyl) B | 4-hydroxyquinolin-2-ol type | yellow |
| 171 | " | 3-hydroxy-N-(4-chlorophenyl)-2-naphthamide | red |
| 172 | " | 3-hydroxy-N-(2-methoxyphenyl)-2-naphthamide | red |
| 173 | (2-aminophenyl)-oxadiazole-phenyl-CONH-(4-Cl-phenyl) A | CH3, CN, OH, N, OH pyridone | yellow |
| 174 | " | 3-hydroxy-N-phenyl-2-naphthamide | red |
| 175 | (2-amino-4-nitrophenyl)-oxadiazole-phenyl-CONH-(4-Cl-phenyl) A | CH3COCH2CONH—⟨phenyl⟩—NHCOCH3 | yellow |
| 176 | " | 3-hydroxy-N-phenyl-2-naphthamide | red |
| 177 | " | 3-hydroxy-N-(2-methoxyphenyl)-2-naphthamide | red |
| 178 | (2-aminophenyl)-oxadiazole-(N-phenylisoindoline-1,3-dione) A | CH3, CN, OH, N, OH pyridone | yellow |
| 179 | " | CH3COCH2CONH—⟨phenyl(NH-acetyl)⟩—NH | yellow |
| 180 | " | 3-hydroxy-N-(2-methoxyphenyl)-2-naphthamide | red |
| 181 | " | 3-hydroxy-N-(4-chlorophenyl)-2-naphthamide | red |
| 182 | (2-amino-5-nitrophenyl)-oxadiazole-(N-phenylisoindoline-1,3-dione) A | CH3COCH2CONH—⟨phenyl⟩—NHCOCH3 | yellow |
| 183 | " | 3-hydroxy-N-(4-chlorophenyl)-2-naphthamide | red |
| 184 | " | 3-hydroxy-N-(2-methylphenyl)-2-naphthamide | red |

-continued

| Ex. No. | Diazo component | Coupling component | Hue |
|---|---|---|---|
| 185 | 2-amino-5-nitrophenyl oxadiazole linked to 2-(2,5-dichlorophenyl)isoquinoline-1,3-dione (A) | 3-hydroxy-N-(4-chlorophenyl)-2-naphthamide | red |
| 186 | 2-aminophenyl oxadiazole linked to phenyl-2-isoquinoline-1,3-dione (A) | 4-methyl-3-cyano-6-hydroxy-2-hydroxy pyridine derivative | yellow |
| 187 | " | 3-hydroxy-N-(2,4-dimethoxyphenyl)-2-naphthamide | red |
| 188 | " | 3-hydroxy-N-(5-chloro-2,4-dimethoxyphenyl)-2-naphthamide | red |
| 189 | 2-amino-5-nitrophenyl oxadiazole linked to phenyl-2-isoquinoline-1,3-dione (A) | 3-hydroxy-N-[3-(1,3-dioxoisoquinolin-2-yl)phenyl]-2-naphthamide | red |
| 190 | " | 3-hydroxy-N-(2-methoxyphenyl)-2-naphthamide | red |
| 191 | 2-amino-5-trifluoromethylphenyl oxadiazole linked to phenyl-2-isoquinoline-1,3-dione (A) | 3-hydroxy-N-(4-chlorophenyl)-2-naphthamide | red |
| 192 | 2-aminophenyl oxadiazole linked to phenyl-NHCO-phenyl (A) | 4-methyl-3-cyano-6-hydroxy-2-hydroxy pyridine derivative | yellow |
| 193 | " | CH₃COCH₂CONH—phenyl(NHCOCH₃)₂ derivative | yellow |
| 194 | " | 3-hydroxy-N-(2-methoxyphenyl)-2-naphthamide | red |
| 195 | " | 3-hydroxy-N-(4-chlorophenyl)-2-naphthamide | red |
| 196 | 2-amino-5-nitrophenyl oxadiazole linked to phenyl-NHCO-phenyl (A) | CH₃-C(=N-NH-C₆H₄-Cl)-CH₂-C(=O)- | yellow |
| 197 | " | 3-hydroxy-N-(4-chlorophenyl)-2-naphthamide | red |

-continued

| Ex. No. | Diazo component | Coupling component | Hue |
|---|---|---|---|
| 198 | 2-amino-4-(trifluoromethyl)-phenyl / 1,2,4-oxadiazole with phenyl-NHCO-A substituent (CF₃, NH₂ on ring) | 3-hydroxy-2-naphthoyl-NH-(2-methoxyphenyl) | red |
| 199 | " | CH₃COCH₂CONH—phenyl | yellow |
| 200 | 2-amino-phenyl 1,2,4-oxadiazole with phenyl-NHCO-A | 3-cyano-6-hydroxy-4-methyl-2-hydroxy-pyridine | yellow |
| 201 | " | 3-hydroxy-2-naphthoyl-NH-(4-chlorophenyl) | red |
| 202 | 5-nitro-2-amino-phenyl 1,2,4-oxadiazole with phenyl-NHCO-A (O₂N, NH₂) | 3-hydroxy-2-naphthoyl-NH-phenyl | red |
| 203 | " | 3-hydroxy-2-naphthoyl-NH-(2-methylphenyl) | red |
| 204 | 5-nitro-2-amino-phenyl 1,2,4-oxadiazole with (OCH₃) phenyl-NHCO-(4-chloro-3-methoxyphenyl) A (O₂N, NH₂) | 3-hydroxy-2-naphthoyl-NH-(4-chlorophenyl) | red |
| 205 | " | 3-hydroxy-2-naphthoyl-NH-(2,5-dimethoxy-4-chlorophenyl) | red |
| 206 | 5-amino-1,3-bis(3-phenyl-1,2,4-oxadiazol-5-yl)benzene B | 3-cyano-6-hydroxy-4-methyl-2-hydroxy-pyridine | yellow |
| 207 | " | CH₃COCH₂CONH—C₆H₄—NHCOCH₃ | yellow |
| 208 | 5-amino-1,3-bis(3-phenyl-1,2,4-oxadiazol-5-yl)benzene B | 3-hydroxy-2-naphthoyl-NH-phenyl | red |
| 209 | " | 3-hydroxy-2-naphthoyl-NH-(2,4,5-trichlorophenyl) | red |
| 210 | " | 3-hydroxy-2-naphthoyl-NH-(2,5-dimethoxy-4-chlorophenyl) | red |
| 211 | 5-amino-2-nitro-1,3-bis(3-phenyl-1,2,4-oxadiazol-5-yl)benzene B | CH₃COCH₂CONH—C₆H₄—NHCOCH₂· (acetoacetylamino-acetylamino-phenylene) | yellow |

-continued
| Ex. No. | Diazo component | Coupling component | Hue |
|---|---|---|---|
| 212 | " | 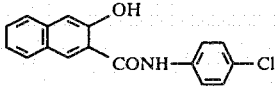 | red |
| 213 | 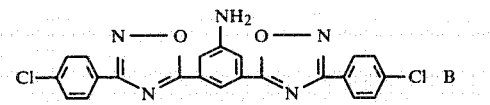 B | 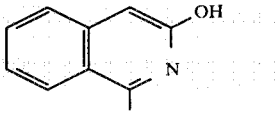 | yellow |
| 214 | " | 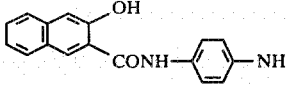 | red |
| 215 | 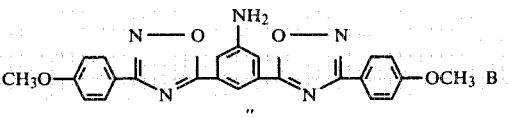 B | 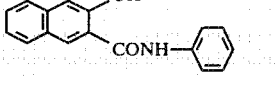 | red |
| 216 | " | 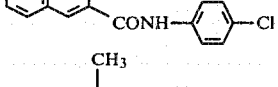 | red |
| 217 | 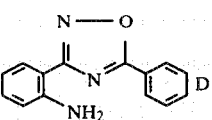 D | 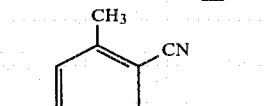 | yellow |
| 218 | " | CH$_3$COCH$_2$CONH—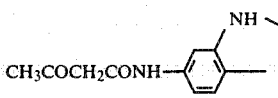—NH—CO—CH$_3$ (NH) | yellow |
| 219 | " | 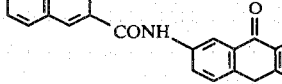 | red |
| 220 | 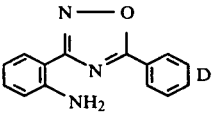 D | 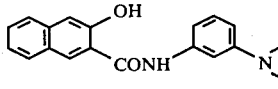 | red |
| 221 | 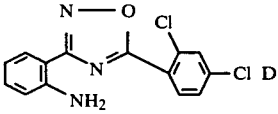 D | 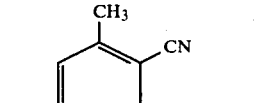 | yellow |
| 222 | " | 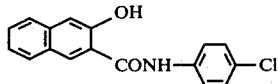 | red |
| 223 | 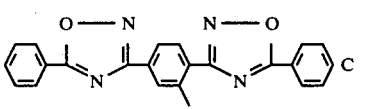 C | 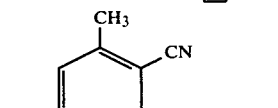 | yellow |
| 224 | " | CH$_3$COCH$_2$CONH—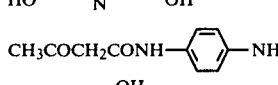—NHCOCH$_3$ | yellow |
| 225 | " | 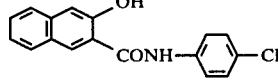 | red |
| 226 | 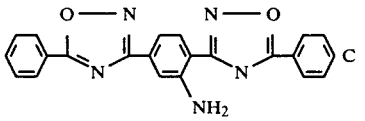 C | 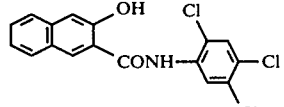 | red |

| Ex. No. | Diazo component | Coupling component | Hue |
|---|---|---|---|
| 227 | " | 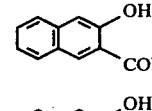 | red |
| 228 | 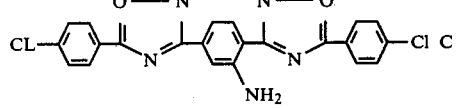 | 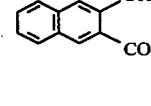 | red |
| 229 | " | 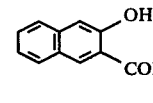 | red |
| 230 | 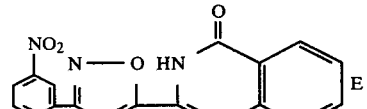 | 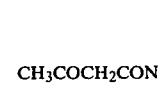 | yellow |
| 231 | " | 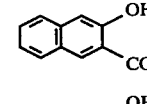 | red |
| 232 | 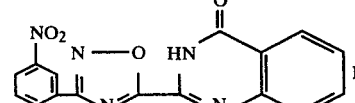 | 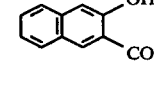 | red |
| 233 | 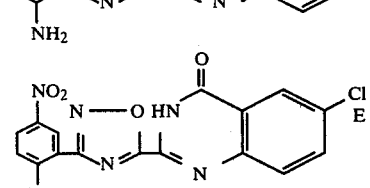 | 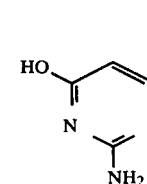 | yellow |
| 234 | " | 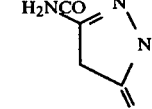 | yellow |
| 235 | " | 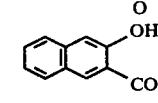 | red |
| 236 | 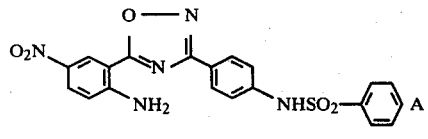 | 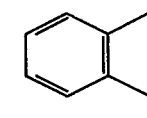 | yellow |
| 237 | 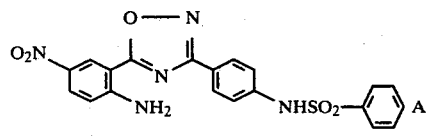 | 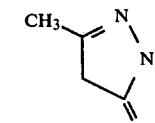 | yellow |
| 238 | " | 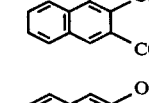 | red |
| 239 | " | 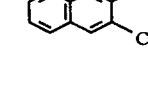 | red |

-continued

| Ex. No. | Diazo component | Coupling component | Hue |
|---|---|---|---|
| 240 | 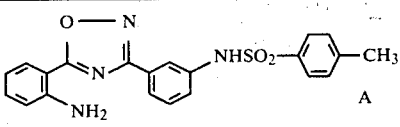 | 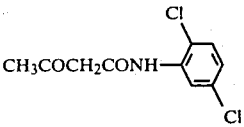 | yellow |
| 241 | " | 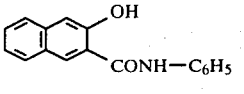 | red |
| 242 | 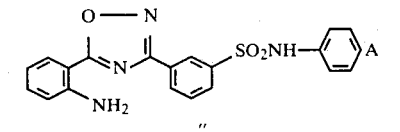 | 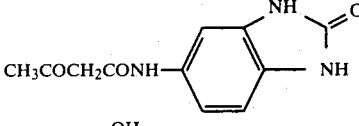 | yellow |
| 243 | " | 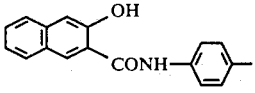 | red |
| 244 | 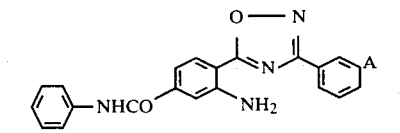 | 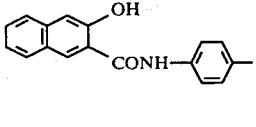 | red |
| 245 | 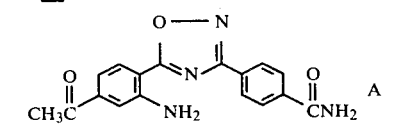 | 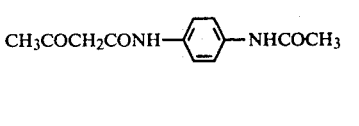 | yellow |
| 246 | 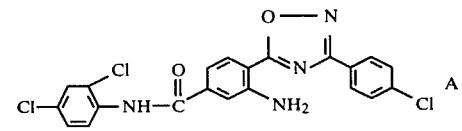 | 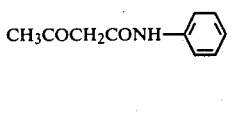 | yellow |
| 247 | 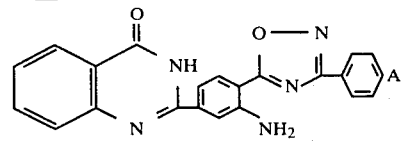 | 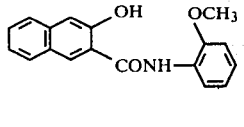 | red |
| 248 | " | 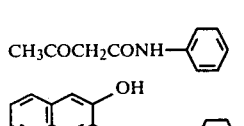 | yellow |
| 249 | 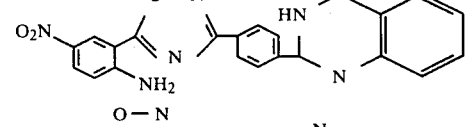 | 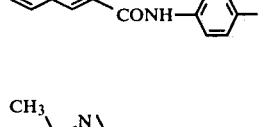 | red |
| 250 | 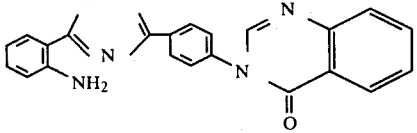 | 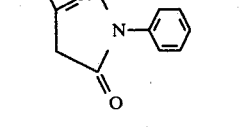 | yellow |
| 251 | " | 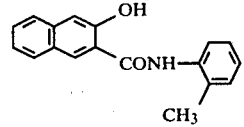 | red |

EXAMPLE 252

The procedure followed is as in Example 1, except that 47 parts of β-hydroxynaphthoic acid are used as the coupling component. After completion of coupling, the mixture is acidified to pH 1 with dilute sulfuric acid and the product is filtered off, washed thoroughly with water and dried. This gives 106 parts of the acid

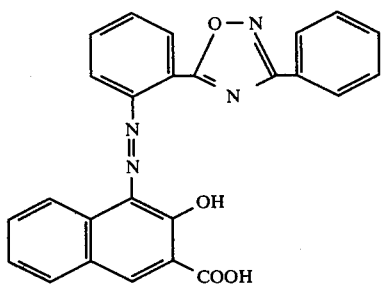

437 Parts of this acid in 1,800 parts of dichlorobenzene, 2 parts of dimethylformamide and 350 parts of thionyl chloride are heated for one hour at 100° C., 2 hours at 115° C. and 1 hour at 125° C. and then cooled; the product is filtered off, washed with toluene and dried. This gives 336 parts of the acid chloride.

22.3 parts of this acid chloride are introduced into 200 parts of nitrobenzene, 22 parts of p-aminobenzanilide are added and the mixture is stirred for 1 hour at 90° C., 1 hour at 110° C. and 2 hours at 130° C. The product is then filtered off at 60° C., washed with nitrobenzene and methanol and dried. This gives 36 parts of a red powder of the formula

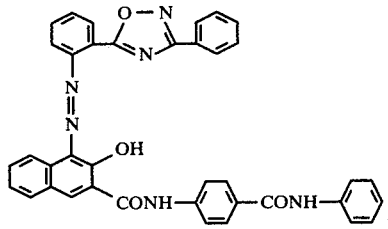

EXAMPLES 253–300

The dyes shown in the table which follows, and having the stated hue, are obtained analogously to Example 252 from the carboxylic acid chlorides, and amines also shown in the table.

| Example No. | Carboxylic acid chloride | Amine | Hue |
|---|---|---|---|
| 253 | (structure as shown) | $NH_2$—C$_6$H$_4$—CO—NH—C$_6$H$_3$(Cl)(Cl) (2,5-dichloro) | red |
| 254 | " | $NH_2$—C$_6$H$_4$—CO—NH—C$_6$H$_3$(Cl)(Cl) (2,4-dichloro) | red |
| 255 | " | $NH_2$—C$_6$H$_4$—CO—NH—C$_6$H$_4$—Cl (3-chloro) | red |
| 256 | " | $NH_2$—C$_6$H$_4$—CO—NH—C$_6$H$_4$—N(phthalimide) (4-) | red |
| 257 | " | $NH_2$—C$_6$H$_4$—CO—NH—C$_6$H$_4$—N(phthalimide) (3-) | red |
| 258 | " | $NH_2$—C$_6$H$_4$—CO—NH—C$_6$H$_3$(OCH$_3$)—N(phthalimide) | red |
| 259 | " | $NH_2$—C$_6$H$_4$—CO—NH—C$_6$H$_3$(CH$_3$)(dihydroquinolinone) | red |

| Example No. | Carboxylic acid chloride | Amine | Hue |
|---|---|---|---|
| 260 | " | NH₂–C₆H₄–CONH–C₆H₄–CONH–C₆H₅ | red |
| 261 | " | 4-aminobenzamide of 2-aminoanthraquinone | red |
| 262 | " | 3-aminobenzoyl-(2,5-dichloroanilide) | red |
| 263 | " | 3-amino-N-[4-(phthalimido)phenyl]benzamide | red |
| 264 | " | 3-aminobenzamide of 2-aminoanthraquinone | red |
| 265 | " | 5-amino-2-chloro-N-[4-(benzoylamino)phenyl]benzamide | red |
| 266 | " | 4-amino-2-chloro-N-[4-(benzoylamino)phenyl]benzamide | red |
| 267 | 1-[(4-nitro-2-(3-phenyl-1,2,4-oxadiazol-5-yl)phenyl)azo]-2-hydroxy-3-naphthoyl chloride | 5-amino-2-methoxy-N-[4-(benzoylamino)phenyl]benzamide | red |
| 268 | " | 5-amino-2-methoxy-N-[4-(phthalimido)phenyl]benzamide | red |
| 269 | " | 5-amino-2,4-dichloro-N-[4-(phthalimido)phenyl]benzamide | red |
| 270 | " | 5-amino-2-methyl-N-(2,5-dichlorophenyl)benzamide | red |

-continued

| Example No. | Carboxylic acid chloride | Amine | Hue |
|---|---|---|---|
| 271 | " | NH₂—⬡(OCH₃)—CO—NH—⬡—CO—NH—⬡ | red |
| 272 | " | NH₂—⬡—CO—NH—⬡—SO₂NH₂ | red |
| 273 | " | NH₂—⬡—CO—NH—⬡(Cl)—SO₂—NH—⬡ | red |
| 274 | " | NH₂—⬡—CO—NH—⬡—SO₂—NH—⬡(Cl, Cl) | red |
| 275 | " | NH₂—⬡—CO—NH—⬡—SO₂—NH—⬡(Cl, Cl) | red |
| 276 | " | NH₂—⬡—CO—NH—⬡—N(CO)₂⬡—CO—NH—⬡ | red |
| 277 | " | NH₂—⬡—NH—CO—⬡ | red |
| 278 | " | NH₂—⬡—NH—CO—⬡—N(CO)₂⬡ | red |
| 279 | " | NH₂—⬡—NH—CO—⬡(Cl, Cl) | red |
| 280 | " | NH₂—⬡(Cl)—NH—CO—⬡(Cl, Cl) | red |
| 281 | " | NH₂—⬡—NH—CO—⬡—(CO)₂N—⬡(Cl, Cl) | red |
| 282 | " | NH₂—⬡(Cl)—NH—CO—⬡—(CO)₂N—⬡—CH₃ | red |

-continued

| Example No. | Carboxylic acid chloride | Amine | Hue |
|---|---|---|---|
| 283 | 5-(2-nitro-4-(3-phenyl-1,2,4-oxadiazol-5-yl)phenylazo)-3-hydroxy-naphthalene-2-carbonyl chloride | 4,5-dichloro-2-[N-(3-methoxyphenyl)phthalimido]aniline derivative | maroon |
| 284 | " | 4-amino-2-methyl-N-(5-chloro-2-methoxyphenyl)phthalimide derivative | red |
| 285 | " | 4-amino-2-methoxy-N-phenylphthalimide derivative | red |
| 286 | " | 4-aminophenyl-N'-phenylurea | maroon |
| 287 | " | 3-amino-N-(4-phthalimidobenzoyl)aniline derivative | — |
| 288 | 5-(2-nitro-4-(3-(4-nitrophenyl)-1,2,4-oxadiazol-5-yl)phenylazo)-3-hydroxy-naphthalene-2-carbonyl chloride | 4-amino-N,N'-diphenyloxamide | red |
| 289 | " | 4-amino-N-(9,10-anthraquinon-2-yl)benzamide | red |
| 290 | " | 4-amino-N-(3-phthalimidobenzoyl)aniline | red |
| 291 | " | 4-amino-2-chloro-N-(3-phthalimidobenzoyl)aniline | red |
| 292 | " | 4-phthalimido-N-(2,4-dichlorophenyl)benzamide derivative | red |

| Example No. | Carboxylic acid chloride | Amine | Hue |
|---|---|---|---|
| 293 | " | NH₂—⟨⟩—CONH—⟨⟩(Cl)—OCH₃ | red |
| 294 | [structure: bis-phenyl-oxadiazolyl benzene with azo-naphthol-COCl] | H₂N—⟨⟩(NO₂)—CH₃ | reddish orange |
| 295 | " | H₂N—⟨⟩—SO₂NH₂ | reddish orange |
| 296 | " | H₂N—⟨⟩—NHCO—⟨⟩(Cl)—Cl | red |
| 297 | " | H₂N—⟨⟩—CONH—⟨⟩(Cl)—OCH₃ | red |
| 298 | " | NH₂—⟨⟩—CO—NH—⟨⟩—N(phthalimide) | reddish orange |
| 299 | " | NH₂—⟨⟩—NH—CO—⟨⟩—N(phthalimide) | red |
| 300 | " | NH₂—⟨⟩—NH—CO—⟨phthalimide⟩—N—⟨⟩—Cl | red |

EXAMPLE 301

84 Parts of benzoyl chloride are added dropwise to a suspension of 60 parts of nitroterephthalic acid dihydrazide in 250 parts to toluene at room temperature, and after one hour a solution of 53 parts of sodium hydroxide in 450 parts of water is added. The mixture is stirred for a further hour and is then acidified and the product is filtered off, washed with alcohol and with water and dried. 88.6 parts of nitroterephthalic acid N',N'-dibenzoyl-dihydrazide of melting point 295°-298° are obtained.

624 Parts of nitroterephthalic acid N',N'-dibenzoyl-dihydrazide are dissolved in 4,000 parts of dimethylformamide at 80° C. and hydrogenated in the presence of Raney nickel. The mixture is filtered hot and the product is precipitated with water, filtered off, washed with water and dried. 530 Parts of aminoterephthalic acid N',N'-dibenzoyl-dihydrazide of melting point 305° are obtained.

530 Parts of aminoterephthalic acid N',N'-dibenzoyl-dihydrazide in 2,000 parts of POCl₃ are heated under reflux until a clear solution has been produced. After cooling, the product is precipitated by pouring the mixture onto ice and is filtered off, washed with water and dried. 490 parts of 2,5-bis-[5-phenyl-1,3,4-oxidiazolyl]-aniline of melting point 294° are obtained.

38.1 Parts of 2,5-bis-[5-phenyl-1,3,4-oxdiazolyl]-aniline are introduced into 200 parts of a 1:1 mixture of glacial acetic acid and propionic acid, cooled to from 0 to 5° C. and diazotized, at this temperature, by adding 30 parts by volume of nitrosylsulfuric acid. The mixture is stirred for 4 hours at 5° C., 50 parts of urea are then added, and a solution of 29.7 parts of β-hydroxynaphthoic acid p-chloroanilide in 300 parts of dimethylformamide and 98 parts of triethanolamine is added dropwise at a rate such that the temperature does not rise above 15° C. The mixture is then stirred for 10 hours at room temperature and 1 hour at 70° C. and the product is filtered off hot and washed thoroughly with dimethylformamide and with water. The paste obtained is added to 400 parts of methanol, the mixture is heated under reflux for one hour and the product is filtered off hot, washed with methanol and dried.

46 Parts of a bluish red powder of the formula

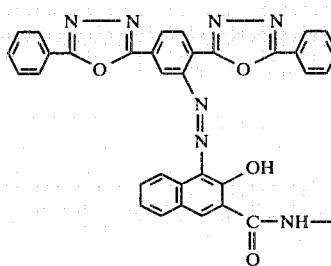

are obtained.

EXAMPLES 302–321

Analogously to Example 301, the coupling components shown in the table which follows give the corresponding dyes, having the hue shown in the table.

| Example No. | Coupling component | Hue |
|---|---|---|
| 302 | | bluish red |
| 303 | | red |
| 304 | | red |
| 305 | | red |
| 306 | | reddish orange |
| 307 | | red |
| 308 | | bluish red |
| 309 | | reddish brown |
| 310 | | reddish brown |

| Example No. | Coupling component | Hue |
|---|---|---|
| 311 | 3-hydroxy-2-naphthoic acid anilide with Cl, OCH₃, OC₂H₅ substituents | reddish brown |
| 312 | 3-hydroxy-2-naphthoic acid 2,5-dimethoxyanilide | red |
| 313 | 3-hydroxy-2-naphthoic acid 2-ethoxyanilide | red |
| 314 | 3-hydroxy-2-naphthoic acid arylide with benzoyl-isoquinolinedione-(2-methoxy-5-chlorophenyl) substituent | red |
| 315 | 3-methyl-1-(2,5-dichlorophenyl)-5-pyrazolone | yellow |
| 316 | 3-methyl-1-(4-sulfamoylphenyl)-5-pyrazolone | yellow |
| 317 | 3-cyano-4-methyl-2,6-dihydroxypyridine | yellow |
| 318 | 2,4-dihydroxyquinoline | yellow |
| 319 | 2-amino-4,6-dihydroxypyrimidine | yellow |
| 320 | H₃C—CO—CH₂—CO—NH—C₆H₅ | yellow |

| Example No. | Coupling component | Hue |
|---|---|---|
| 321 | H₃C—C(=O)—CH₃—C(=O)—NH—C₆H₄—(OCH₃)$_p$ | yellow |

EXAMPLE 322

22.5 Parts of 2,5-bis-[5-(p-chlorophenyl)-1,3,4-oxidiazolyl]-aniline are introduced into 200 parts of a 1:1 mixture of glacial acetic acid and propionic acid, cooled to from 0° to 5° C. and diazotized, at this temperature, by adding 15 parts of volume of nitrosylsulfuric acid. The mixture is stirred for one hour, 270 parts of sulfuric acid are added to produce complete solution, and the mixture is then stirred for a further 4 hours. Thereafter the product is precipitated by pouring the mixture onto ice, 25 parts of urea are added to the batch and the product is filtered off. The filter cake is worked into a paste with dimethylformamide and this paste is added to a solution of 14.87 parts of β-hydroxynaphthoic acid p-chloroanilide in 500 parts of dimethylformamide. The pH is brought to from 5 to 6 by adding pyridine. The mixture is stirred overnight and the product is then filtered off and washed with dimethylformamide, water and methanol. After drying, 33.6 parts of a red powder of the formula

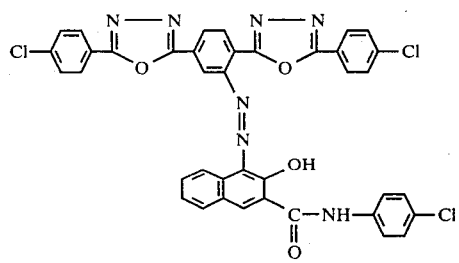

are obtained.

The coupling components listed in the table which follows analogously give the corresponding dyes;

| Example No. | Coupling component | Hue |
|---|---|---|
| 323 | 3-hydroxy-2-naphthoic acid anilide | red |
| 324 | 3-hydroxy-2-naphthoic acid p-methoxyanilide | red |
| 325 | 3-hydroxy-2-naphthoic acid 1-naphthylamide | red |
| 326 | 3-hydroxy-2-naphthoic acid 2-naphthylamide | red |
| 327 | 3-hydroxy-2-naphthoic acid 2-methylanilide | reddish orange |
| 328 | 3-hydroxy-2-naphthoic acid (2-methyl-5-chloro)anilide | red |
| 329 | 3-hydroxy-2-naphthoic acid 3-nitroanilide | red |
| 330 | 3-hydroxy-2-naphthoic acid (2-methyl-4-methoxy)anilide | red |
| 331 | 3-hydroxy-2-naphthoic acid 2-methoxyanilide | reddish orange |
| 332 | 3-hydroxy-2-naphthoic acid (2-chloro-4-methoxy-5-ethoxy)anilide | red |
| 333 | 3-hydroxy-2-naphthoic acid 2-methoxyanilide | red |
| 334 | 3-hydroxy-2-naphthoic acid (2-chloro-4-methoxy-5-ethoxy)anilide | red |
| 335 | 3-hydroxy-2-naphthoic acid (2-methoxy-4-methoxy)anilide | red |
| 336 | 3-hydroxy-2-naphthoic acid 2-ethoxyanilide | red |

-continued

| Example No. | Coupling component | Hue |
|---|---|---|
| 337 | (5-methyl-3-oxo-1-(2,5-dichlorophenyl)-2-pyrazoline) | yellow |
| 338 | (5-methyl-3-oxo-1-(4-sulfamoylphenyl)-2-pyrazoline) | yellow |
| 339 | (4-methyl-3-cyano-2,6-dihydroxypyridine) | yellow |
| 340 | (4-hydroxy-2-quinolone) | yellow |
| 341 | (2-amino-4,6-dihydroxypyrimidine) | yellow |

EXAMPLE 342–349

The procedure followed is as in Example 22, except that the diazo component is 3,5-bis-[5-phenyl-1,3,4-oxdiazoyl]-aniline and the coupling components shown in the table are used. The corresponding dyes, having the hue shown in the table, as obtained:

| Example No. | Coupling component | Hue |
|---|---|---|
| 342 | (3-hydroxy-2-naphthoyl-4-chloroanilide) | reddish orange |
| 343 | (3-hydroxy-2-naphthoyl-anilide) | reddish orange |
| 344 | (3-hydroxy-2-naphthoyl-4-methoxyanilide) | reddish orange |

-continued

| Example No. | Coupling component | Hue |
|---|---|---|
| 345 | (5-methyl-3-oxo-1-(2,5-dichlorophenyl)-2-pyrazoline) | yellow |
| 346 | (5-methyl-3-oxo-1-(4-sulfamoylphenyl)-2-pyrazoline) | yellow |
| 347 | (4-methyl-3-cyano-2,6-dihydroxypyridine) | greyish yellow |
| 348 | (4-hydroxy-2-quinolone) | yellow |
| 349 | (2-amino-4,6-dihydroxypyrimidine) | yellow |

EXAMPLE 350–367

The procedure followed is as in Example 322, except that the diazo component is 2,5-bis-[5(p-methoxyphenyl)-1,3,4-oxdiazoyl]-aniline and the coupling components shown in the table are used. The corresponding dyes, having the hue shown in the table, are obtained:

| Example No. | Coupling component | Hue |
|---|---|---|
| 350 | (3-hydroxy-2-naphthoyl-4-chloroanilide) | reddish brown |
| 351 | (3-hydroxy-2-naphthoyl-anilide) | reddish brown |
| 352 | (3-hydroxy-2-naphthoyl-4-methoxyanilide) | red |

-continued

| Example No. | Coupling component | Hue |
|---|---|---|
| 353 | (3-hydroxy-2-naphthoyl)-NH-(1-naphthyl) | bluish red |
| 354 | (3-hydroxy-2-naphthoyl)-NH-(2-naphthyl) | red |
| 355 | (3-hydroxy-2-naphthoyl)-NH-(2-methylphenyl) | red |
| 356 | (3-hydroxy-2-naphthoyl)-NH-(2-methyl-5-chlorophenyl) | red |
| 357 | (3-hydroxy-2-naphthoyl)-NH-(3-nitrophenyl) | red |
| 358 | (3-hydroxy-2-naphthoyl)-NH-(2-methyl-4-methoxyphenyl) | red |
| 359 | (3-hydroxy-2-naphthoyl)-NH-(2-methoxyphenyl) | red |
| 360 | (3-hydroxy-2-naphthoyl)-NH-(5-chloro-4-methoxy-2-ethoxyphenyl) | red |
| 361 | (3-hydroxy-2-naphthoyl)-NH-(2,5-dimethoxyphenyl) | red |
| 362 | (3-hydroxy-2-naphthoyl)-NH-(2-ethoxyphenyl) | red |
| 363 | pyridazinone with 2,5-dichlorophenyl | yellow |
| 364 | pyridazinone with 4-sulfamoylphenyl | yellow |
| 365 | 4-methyl-3-cyano-6-hydroxy-2-hydroxypyridine | yellow |
| 366 | 2-amino-4,6-dihydroxypyrimidine derivative | greenish yellow |

EXAMPLES 367–383

The procedure followed is as in Example 322, except that the diazo component is 2,5-bis-[5(2,4-dichlorophenyl)-1,3,4-oxdiazolyl]-aniline and the coupling components shown in the table are used. The corresponding dyes, having the hue shown in the table, are obtained:

| Example No. | Coupling component | Hue |
|---|---|---|
| 367 | (3-hydroxy-2-naphthoyl)-NH-(4-chlorophenyl) | red |
| 368 | (3-hydroxy-2-naphthoyl)-NH-phenyl | reddish brown |
| 369 | (3-hydroxy-2-naphthoyl)-NH-(4-methoxyphenyl) | brown |
| 370 | (3-hydroxy-2-naphthoyl)-NH-(1-naphthyl) | red |
| 371 | (3-hydroxy-2-naphthoyl)-NH-(2-naphthyl) | red |
| 372 | (3-hydroxy-2-naphthoyl)-NH-(2-methylphenyl) | reddish brown |

-continued

| Example No. | Coupling component | Hue |
|---|---|---|
| 373 | 3-hydroxy-N-(5-chloro-2-methylphenyl)-2-naphthalenecarboxamide | reddish brown |
| 374 | 3-hydroxy-N-(3-nitrophenyl)-2-naphthalenecarboxamide | red |
| 375 | 3-hydroxy-N-(4-methoxy-2-methylphenyl)-2-naphthalenecarboxamide | red |
| 376 | 3-hydroxy-N-(2-methoxyphenyl)-2-naphthalenecarboxamide | red |
| 377 | 3-hydroxy-N-(2-chloro-4-methoxy-5-ethoxyphenyl)-2-naphthalenecarboxamide | red |
| 378 | 3-hydroxy-N-(2,5-dimethoxyphenyl)-2-naphthalenecarboxamide | reddish brown |
| 379 | 3-hydroxy-N-(2-ethoxyphenyl)-2-naphthalenecarboxamide | reddish brown |
| 380 | 1-(2,5-dichlorophenyl)-3-methyl-5-pyrazolone | yellow |
| 381 | 1-(4-sulfamoylphenyl)-3-methyl-5-pyrazolone | yellow |
| 382 | 4-methyl-3-cyano-2,6-dihydroxypyridine | yellow |
| 383 | 2-amino-4,6-dihydroxypyrimidine | yellow |

EXAMPLE 384–386

The procedure followed is as in Example 301, except that the diazo component is 2,5-bis-[-5-(α-naphthyl)-1,3,4-oxdizolyl]-aniline and the coupling components shown in the table are used. The corresponding dyes, having the hue shown in the table, are obtained:

| Example No. | Coupling component | Hue |
|---|---|---|
| 384 | 3-hydroxy-N-(4-chlorophenyl)-2-naphthalenecarboxamide | red |
| 385 | 3-hydroxy-N-phenyl-2-naphthalenecarboxamide | red |
| 386 | 3-hydroxy-N-(4-methoxyphenyl)-2-naphthalenecarboxamide | red |

EXAMPLES 387–392

The procedure followed is as in Example 301, except that the diazo component is 3,5-bis[-5-(β-naphthyl)-1,3,4-oxdiazolyl]-aniline and the coupling components shown in the table are used. The corresponding dyes, having the hue shown in the table, are obtained:

| Ex. No. | Coupling component | Hue |
|---|---|---|
| 387 | 3-hydroxy-N-(4-chlorophenyl)-2-naphthalenecarboxamide | red |
| 388 | 3-hydroxy-N-phenyl-2-naphthalenecarboxamide | red |
| 389 | 3-hydroxy-N-(4-methoxyphenyl)-2-naphthalenecarboxamide | red |

| Ex. No. | Coupling component | Hue |
|---|---|---|
| 390 | 3-hydroxy-N-(1-naphthyl)-2-naphthamide | red |
| 391 | 3-hydroxy-N-(2-naphthyl)-2-naphthamide | red |
| 392 | 3-hydroxy-N-(2-methylphenyl)-2-naphthamide | red |

EXAMPLE 393-394

4-Chloro-2,5-bis-5-phenyl-1,3,4-oxdiazolyl-aniline is prepared analogously to Example 301 from 3-chloro-6-nitroterephthalic acid dihydrazide and is diazotized, and coupled, as described in Example 301. Using the coupling components shown in the table, the corresponding dyes, having the hue shown in the table, are obtained:

| Ex. No. | Coupling component | Hue |
|---|---|---|
| 393 | 3-hydroxy-N-(4-chlorophenyl)-2-naphthamide | red |
| 394 | 3-hydroxy-N-phenyl-2-naphthamide | red |

EXAMPLES 395-401

3,5-bis-[5-p-chlorophenyl-1,3,4-oxdiazolyl]-aniline is prepared analogously to Example 301 and is diazotized, and coupled, as indicated in Example 322. Using the coupling components shown in the table which follows, the corresponding dyes, having the hue shown in the table, are obtained:

| Example No. | Coupling component | Hue |
|---|---|---|
| 395 | 3-hydroxy-N-(4-chlorophenyl)-2-naphthamide | red |
| 396 | 3-hydroxy-N-phenyl-2-naphthamide | red |
| 397 | 3-hydroxy-N-(4-methoxyphenyl)-2-naphthamide | red |
| 398 | 3-methyl-1-(2,5-dichlorophenyl)-5-pyrazolone | yellow |
| 399 | 3-methyl-1-(4-sulfamoylphenyl)-5-pyrazolone | yellow |
| 340 | 4-methyl-3-cyano-2,6-dihydroxypyridine | yellow |
| 401 | 2,4-dihydroxyquinoline | yellow |

EXAMPLE 402

94.8 Parts of 2,5-bis-[5-phenyl-1,3,4-oxdiazolyl]-aniline are introduced into 500 parts of concentrated sulfuric acid at from 10° to 15° C. and after cooling from 0° to 5° C. are diazotized by adding 75 ccs of nitrosylsulfuric acid. The mixture is stirred for 5 hours and then poured onto 4 kg of ice, and urea is added. 46.1 parts of finely powdered β-hydroxynaphthoic acid are then added, followed by dilute sodium hydroxide solution until the pH is from 6 to 7. After completion of coupling, the mixture is acidified to pH 1 with dilute sulfuric acid and the product is filtered off, washed thoroughly with water and dried. This gives 137 parts of the acid of the formula

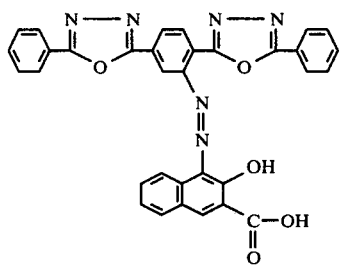

137 Parts of this acid in 1,400 parts of thionyl chloride are heated under reflux for 7 hours. The thionyl chloride is then distilled off and the residue is taken up in petroleum ether, filtered off, washed with petroleum ether and dried. This gives 134 parts of the acid chloride of the formula

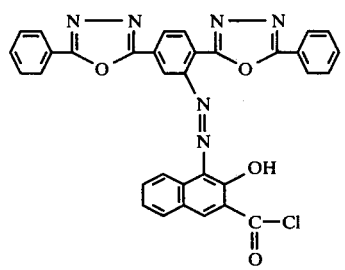

11.9 Parts of this acid chloride are introduced into 150 parts by volume of dry nitrobenzene, 3.24 parts of 3,4-dichloroaniline are added and the mixture is stirred for 1 hour at 110° C. and 4 hours at 130° C. The product is then filtered off, washed with nitrobenzene, dimethylformamide and methanol and dried, giving 3.6 parts of the dye of the formula

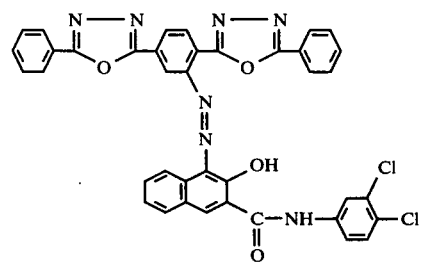

EXAMPLE 403–418

The procedure followed is as in Example 402 except that the amines shown in the table are used in place of 3,4-dichloroaniline. The corresponding dyes, having the hue shown in the table, are obtained:

| Example No. | Amine | Hue |
|---|---|---|
| 403 | 2-NH$_2$-C$_6$H$_4$-C(O)NH$_2$ | reddish orange |
| 404 | 2,4,5-trichloroaniline | red |
| 405 | 2,5-dichloroaniline | reddish orange |
| 406 | 2,4-dichloroaniline | red |
| 407 | 4-aminophenyl-BO$_2$ | bluish red |
| 408 | 2-NO$_2$-4-OCH$_3$-aniline | red |
| 409 | 2-NO$_2$-4-CH$_3$-aniline | red |
| 410 | 3-NO$_2$-4-CH$_3$-aniline | red |
| 411 | 4-SO$_2$NH$_2$-aniline | bluish red |
| 412 | 3-SO$_2$NH$_2$-aniline | reddish orange |

-continued

| Example No. | Amine | Hue |
|---|---|---|
| 413 |  | bluish red |
| 414 | | red |
| 415 |  | reddish orange |
| 416 | | red |
| 417 |  | red |
| 418 | | bluish red |

EXAMPLE 419

800 parts of o-chlorobenzoic acid in 2,400 parts of chlorosulfonic acid are stirred for 10 hours at from 85° to 90° C. The product is then precipitated by pouring the mixture onto ice and is filtered off, washed thoroughly with water and dried. This gives 970 parts of a colorless powder of the formula

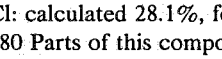

602 Parts of 2-chloro-5-chlorosulfonylbenzoic acid are added to a solution of 830 parts of 2,4-dichloroaniline in 600 parts of toluene at 60° and the mixture is stirred for 6 hours at the same temperature. Insoluble material is then dissolved in dilute sodium hydroxide solution, the aqueous layer is separated off and acidified with dilute hydrochloric acid and the product is filtered off and washed with water. After redissolving in sodium hydroxide solution, reprecipitation with hydrochloric acid and drying, 592 parts of 2-chloro-5-[2,4-dichlorophenyl-sulfamoyl]-benzoic acid are obtained as a colorless powder of melting point 174° C.

Cl: calculated 28.1%, found 28.4%.

280 Parts of this compound, in 1,500 parts of 20 percent strength ammonia, are stirred with 2 parts of copper-(I) chloride for 8 hours at 150° C. After the mixture has cooled, it is acidified and the product is filtered off, washed with water and dried. This gives 246 parts of 5-[2,4-dichlorophenyl-sulfamoyl]-anthranilic acid of melting point 224° C.

Cl: calculated 19.6%, found 19.6%.

179 parts of the above anthranilic acid are suspended in 800 parts of dioxane and phosgene is passed into this suspension for 8 hours at room temperature. The suspension is then purged with nitrogen and the product is filtered off, washed with ice water and dried. This gives 123 parts of 5-[2,4-dichlorophenyl-sulfamoyl] isatoic anhydride of melting point 215° C.

97 Parts of this isatoic anhydride are dissolved in 200 parts of N-methylpyrrolidone and 35 parts of benzhydrazide are added. The mixture is stirred at 120° C. until the evolution of $CO_2$ is ceased, 35 parts of phosphorus pentoxide are then added and the batch is stirred for a further 4 hours at 120° C. After cooling, the product is precipitated with water, filtered off, rinsed with water and dried. This gives 107 parts of 4-[2,4-dichlorophenyl-sulfamoyl]-2 [5-phenyl-1,3,4-oxdiazolyl]-aniline of meltingpoint 215°-220° C.

23 parts of 4-[2,4-dichlorophenyl-sulfamoyl]-2-[5-phenyl-1,3,4-oxdiazolyl]-aniline are added to 300 parts of a 1:1 mixture glacial acetic acid and propionic acid, and are diazotized with 25 parts by volume of nitrosylsulfuric acid at from 0° to 5° C. The mixture is stirred for 4 hours at 5° C., 50 parts of urea are added and a solution of 13.65 parts of β-hydroxynaphthoic acid anilide in 200 parts of methanol and 20 parts of 50% strength sodium hydroxide solution is run in slowly. The pH is brought to from 5 to 6 with dilute sodium hydroxide solution and the mixture is stirred overnight. The product is then filtered off and washed with methanol and with water. The moist paste is stirred with methylglycol at from 90° to 100° C.for one hour and the product is then filtered off hot, washed with methylglycol and water and dried. This gives 28.4 parts of a red powder of the formula

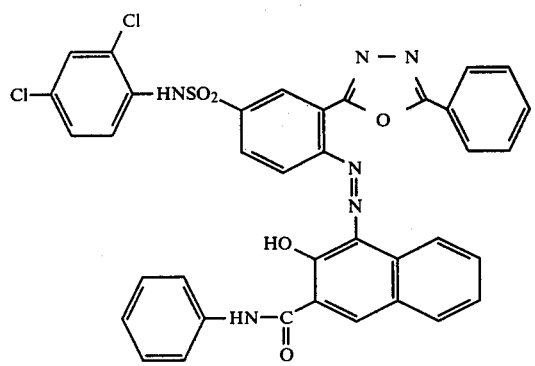

EXAMPLE 420–451

The procedure followed is as in Example 419 but in place of 2,4-dichloroaniline the amines indicated in the table are employed; using the coupling components also shown, the corresponding dyes, having the hue shown in the table, are obtained:

| Example No. | Amine | Coupling component | Hue |
|---|---|---|---|
| 420 | ⟨aniline⟩ | 3-CH, N-(4-chlorophenyl)-2-naphthamide | reddish orange |
| 421 | " | 3-OH, N-phenyl-2-naphthamide | red |
| 422 | " | 3-OH, N-(4-methoxyphenyl)-2-naphthamide | reddish brown |
| 423 | " | 3-methyl-1-(2,5-dichlorophenyl)-5-pyrazolone | greenish yellow |
| 424 | " | 3-methyl-1-(4-sulfamoylphenyl)-5-pyrazolone | greenish yellow |
| 425 | " | 4-methyl-3-cyano-2,6-dihydroxypyridine | greenish yellow |
| 426 | " | 2-amino-4,6-dihydroxypyrimidine | greenish yellow |

-continued

| Example No. | Amine | Coupling component | Hue |
|---|---|---|---|
| 427 | 2,4-dichloroaniline | 3-hydroxy-N-(4-chlorophenyl)-2-naphthamide | reddish orange |
| 428 | " | 3-hydroxy-N-phenyl-2-naphthamide | reddish orange |
| 429 | " | 3-hydroxy-N-(4-methoxyphenyl)-2-naphthamide | reddish brown |
| 430 | " | 3-hydroxy-N-(1-naphthyl)-2-naphthamide | reddish brown |
| 431 | " | 3-hydroxy-N-(2-naphthyl)-2-naphthamide | reddish brown |
| 432 | " | 3-hydroxy-N-(2-methylphenyl)-2-naphthamide | red |
| 433 | " | 1-(2,5-dichlorophenyl)-3-methyl-5-pyrazolone | yellow |
| 434 | " | 1-(4-sulfamoylphenyl)-3-methyl-5-pyrazolone | yellow |
| 435 | " | 3-cyano-4-methyl-2,6-dihydroxypyridine | yellow |
| 436 | 2,5-dichloroaniline | 3-hydroxy-N-(4-chlorophenyl)-2-naphthamide | reddish orange |

-continued
| Example No. | Amine | Coupling component | Hue |
|---|---|---|---|
| 437 | " | 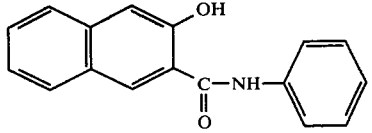 | red |
| 438 | " | 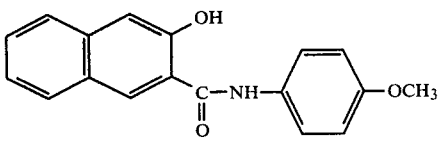 | red |
| 439 | " | 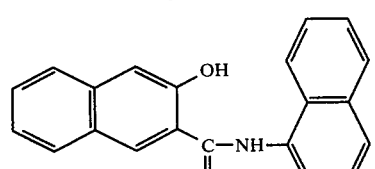 | bluish red |
| 440 | " | 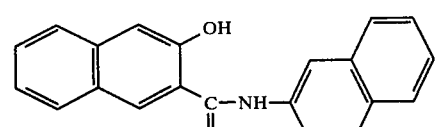 | red |
| 441 | " | 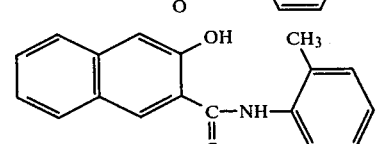 | bluish red |
| 442 | " | 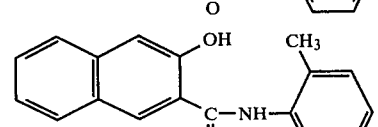 | orange |
| 443 | " | 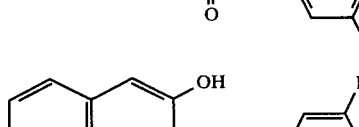 | orange |
| 444 | " | 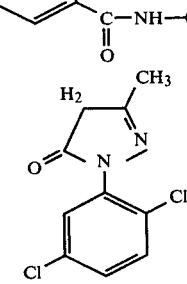 | yellow |
| 445 | " | 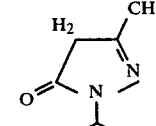 | yellow |
| 446 | " | 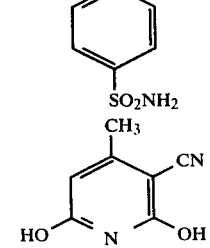 | yellow |

-continued

| Example No. | Amine | Coupling component | Hue |
|---|---|---|---|
| 447 | " | [4-hydroxy-2-hydroxyquinoline structure] | yellow |
| 448 | " | [4,6-dihydroxy-2-aminopyrimidine structure] | greenish yellow |
| 449 | [7-amino-4-methylquinolin-2(1H)-one structure] | [3-hydroxy-N-phenyl-2-naphthamide structure] | red |
| 450 | [2-aminoanthraquinone structure] | [3-hydroxy-N-phenyl-2-naphthamide structure] | red |
| 451 | " | [3-hydroxy-N-(4-chlorophenyl)-2-naphthamide structure] | red |

EXAMPLE 452–457

5-(Phenylcarbamoyl)-2-(5-phenyl-1,3,4-oxdiazolyl)-aniline is prepared analogously to Example 419 from the corresponding 4-phenylcarbamoyl-anthranilic acid and is diazotized and coupled with the coupling components shown in the table. This gives the corresponding dyes, having the hue shown in the table.

| Example No. | Coupling component | Hue |
|---|---|---|
| 452 | [3-hydroxy-N-(4-chlorophenyl)-2-naphthamide] | red |
| 453 | [3-hydroxy-N-phenyl-2-naphthamide] | red |
| 454 | [3-hydroxy-N-(4-methoxyphenyl)-2-naphthamide] | red |
| 455 | [1-(2,5-dichlorophenyl)-3-methyl-5-pyrazolone] | yellow |
| 456 | [1-(4-sulfamoylphenyl)-3-methyl-5-pyrazolone] | yellow |
| 457 | [4-methyl-3-cyano-2,6-dihydroxypyridine] | yellow |

EXAMPLE 458–462

5-(2,5-Dichlorophenylcarbamoyl)-2-(5-phenyl,3,4-oxdiazolyl)aniline is prepared analogously to Example 419 from the corresponding 4-(2,5-dichlorophenylcarbamoyl)-anthranilic acid and is diazotized and coupled with the coupling components shown in the table. This gives the corresponding dyes, having the hue shown in the table:

| Example No. | Coupling component | Hue |
|---|---|---|
| 458 | 3-hydroxy-2-naphthoic acid 4-chloroanilide | red |
| 459 | 3-hydroxy-2-naphthoic acid anilide | red |
| 460 | 3-hydroxy-2-naphthoic acid 4-methoxyanilide | red |
| 461 | 1-(2,5-dichlorophenyl)-3-methyl-5-pyrazolone | yellow |
| 462 | 2,6-dihydroxy-4-methyl-3-cyanopyridine | yellow |

The dyes of the formula I characterized, in the table which follows, by R and by the coupling component, are also obtained analogously to Example 301.

| Example No. | R | Coupling component | Hue |
|---|---|---|---|
| 463 | CH₃ | 3-hydroxy-2-naphthoic acid 4-chloroanilide | red |
| 464 | " | 3-hydroxy-2-naphthoic acid anilide | orange |
| 465 | " | 2,6-dihydroxy-4-methyl-3-cyanopyridine | yellow |
| 466 | " | CH₃COCH₂CONH—C₆H₄—NHCOCH₃ | yellow |
| 467 | CH₂C₆H₅ | 3-hydroxy-2-naphthoic acid anilide | reddish orange |
| 468 | " | 3-hydroxy-2-naphthoic acid 4-chloroanilide | red |
| 469 | 4-methylphenyl | " | bluish red |
| 470 | 2-(NHSO₂C₆H₅)phenyl | " | bluish red |
| 471 | 3-(SO₂NHC₆H₅)phenyl | 3-hydroxy-2-naphthoic acid 4-chloroanilide | bluish red |

| Example No. | R | Coupling component | Hue |
|---|---|---|---|
| 472 | 2-(NHSO₂C₆H₅)-C₆H₄– | 3-hydroxy-2-naphthanilide | red |
| 473 | 4-(NHCOC₆H₅)-C₆H₄– | 3-hydroxy-N-(2-chloro-4-methylphenyl)-2-naphthamide | reddish orange |
| 474 | 4-(NHCOC₆H₅)-C₆H₄– | 1-(2-chlorophenyl)-3-methyl-5-hydroxypyrazole | yellow |
| 475 | 3-(SO₂NHC₆H₅)-C₆H₄– | CH₃COCH₂CONH–C₆H₄–NHCOCH₃ (1,4) | yellow |
| 476 | 4-methyl-2-(benzimidazolinone-type, 2,3-dioxo) phenyl | 3-hydroxy-2-naphthanilide | reddish brown |
| 477 | 4-methyl-2-(benzimidazolinone-type, 2,3-dioxo) phenyl | CH₃COCH₂CONHC₆H₅ | greenish yellow |
| 478 | 2-(benzimidazolin-2-one)-phenyl | CH₃COCH₂CONH–(2-OCH₃)C₆H₄ | yellow |
| 479 | " | 3-hydroxy-N-(4-chlorophenyl)-2-naphthamide | red |
| 480 | " | 3-hydroxy-N-(4-methoxyphenyl)-2-naphthamide | reddish brown |
| 481 | 4-methyl-2-(2-phenyl-2,3-dihydrophthalazine-1,4-dione)phenyl | 3-hydroxy-N-(4-chlorophenyl)-2-naphthamide | bluish red |
| 482 | " | 4-methyl-3-cyano-2,6-dihydroxypyridine | yellow |

-continued

| Example No. | R | Coupling component | Hue |
|---|---|---|---|
| 483 | 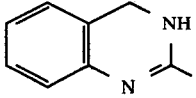 | 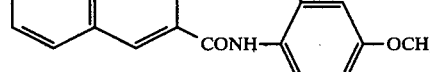 | brown |
| 484 | CONHC$_6$H$_5$ | 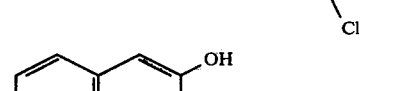 | bluish red |
| 485 | " | 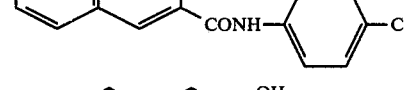 | bluish red |
| 486 | " | 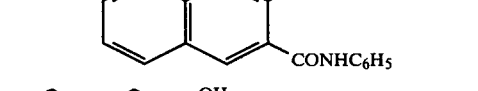 | bluish red |
| 487 | " | 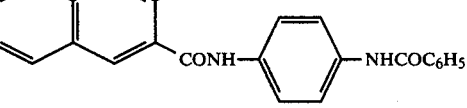 | red |
| 488 | 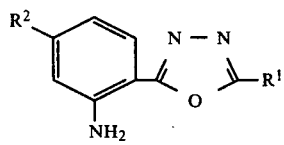 |  | red |

Using the diazo components of the formula

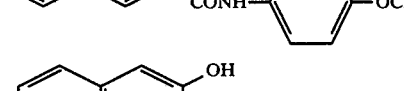

corresponding dyes are obtained analogously to Example 301:

| Example No. | R$^1$ | R$^2$ | Hue |
|---|---|---|---|
| 489 | —C$_6$H$_4$—CH(CH$_3$)$_2$ | N—N, O, —C$_6$H$_4$—CH(CH$_3$)$_2$ | orange |
| 490 | —C$_6$H$_4$—OCH$_3$ | N—N, O, —C$_6$H$_4$—OCH$_3$ | red |
| 491 | —C$_6$H$_4$—C$_6$H$_5$ | N—N, O, —C$_6$H$_4$—C$_6$H$_5$ | red |
| 492 | —C$_6$H$_4$—NH—CO—C$_6$H$_5$ | N—N, O, —C$_6$H$_4$—NH—CO—C$_6$H$_5$ | red |
| 493 | —C$_6$H$_4$—SO$_2$NH$_2$ | N—N, O, —C$_6$H$_4$—SO$_2$NH$_2$ | red |

-continued

| Example No. | R¹ | R² | Hue |
|---|---|---|---|
| 494 | -C₆H₄-NHCO-CH₃ | oxadiazole-C₆H₄-NH-CO-CH₃ | red |
| 495 | -CH=CH-C₆H₅ | oxadiazole-CH=CH-C₆H₅ | red |
| 496 | -C₆H₄-SO₂-NH-C₆H₅ | oxadiazole-C₆H₄-SO₂NH-C₆H₅ | orange |
| 497 | -C₆H₅ | -CONH₂ | red |
| 498 | -C₆H₅ | -CO-NH-(2,5-diCl-C₆H₃) | red |
| 499 | -C₆H₄-Cl | -CONH-C₆H₄-CH₃ | red |
| 500 | -(2,4-diCl-C₆H₃) | -CONH₂ | red |
| 501 | -C₆H₄-Cl | -CONH-C₆H₄-Cl | red |
| 502 | -C₆H₅ | -CONH-C₆H₅ | red |

Analogously to Example 402, the amines shown in the table which follows give the corresponding dyes:

| Example No. | Amine | Hue |
|---|---|---|
| 503 | H₂N-C₆H₄-CH(CH₃)₂ | red |
| 504 | H₂N-C₆H₄-CONH-(2,5-diCl-C₆H₃) | reddish orange |
| 505 | H₂N-C₆H₄-CONH-anthraquinonyl | reddish brown |
| 506 | H₂N-C₆H₄-NH-CO-C₆H₅ | red |
| 507 | H₂N-C₆H₄-NHCO-C₆H₄-Cl | red |
| 508 | H₂N-C₆H₄-NHCO-C₆H₄-CH₃ | red |
| 509 | H₂N-C₆H₄-SO₂-NH₂ | orange |
| 510 | H₂N-C₆H₄-SO₂-NH₂ | red |
| 511 | 7-amino-4-methylcarbostyril | red |
| 512 | 5-amino-2-(methyleneamino)benzamide | bluish red |
| 513 | 2-aminoanthraquinone | red |
| 514 | H₂N-C₆H₄-CONH-C₆H₄-OCH₃ | orange |
| 515 | H₂N-C₆H₄-CONH-C₆H₄-CH₃ | red |
| 516 | 3-amino-4-chloro-phenyl phthalazinone | reddish orange |

-continued

| Example No. | Amine | Hue |
|---|---|---|
| 517 | H₂N—⟨⟩—NH—COCH₃ | red |

The following coupling components can also be used analogously to Example 301:

| Ex. No. | Coupling component | Hue |
|---|---|---|
| 518 | H₃C—COCH₂—CONH—⟨⟩ | greenish yellow |
| 519 | H₃C—COCH₂—CONH—⟨⟩—Cl | greenish yellow |
| 520 | H₃C—COCH₂—CONH—⟨⟩—NHCOCH₃ | yellow |
| 521 | H₃C—COCH₂—CONH—⟨⟩—NHCO—⟨⟩ | yellow |
| 522 | H₃C—COCH₂—CONH—⟨⟩(CH₃)—CH₃ | greenish yellow |
| 523 | H₃C—COCH₂—CONH—⟨⟩—OCH₃ | yellow |
| 524 | H₃C—COCH₂—CONH—⟨⟩—N(phthalimide) | yellow |
| 525 | H₃C—COCH₂—CONH—(4-methylquinolin-2(1H)-one) | greenish yellow |
| 526 | H₃C—COCH₂—CONH—(quinazolinone) | greenish yellow |
| 527 | 3-hydroxy-2-naphthoyl-NH—(2-chlorophenyl) | red |
| 528 | 3-hydroxy-2-naphthoyl-NH—(2,5-dichlorophenyl) | red |
| 529 | 3-hydroxy-2-naphthoyl-NH—(3-chlorophenyl) | red |

Use

EXAMPLE 1

In surface coatings

5 Parts of the dye obtained according to Example 2 and 95 parts of a baking finish (eg. 70% of coconut alkyd resin in the form of a 60% strength solution in xylene, and 30% of melamine resin in the form of a solution of about 55% strength in butanol/xylene) are milled in an attrition mill. After applying a coat of the mixture and baking this for 30 minutes at 120° C., brilliant richly colored surface coatings of very good fastness to light and to over-coating are obtained.

Brilliant whitening effects are achieved by addition of, eg., TiO₂.

EXAMPLE 2

In plastics

Deep, light-fast and above all brilliant colorations of plasticized PVC are achieved by working, eg., 0.05 part of the organic pigment obtained according to Example 1 into 50 parts of a plasticized PVC mixture consisting of 65 parts of PVC powder (eg. Vinoflex 531 (a registered tradename)), 35 parts of plasticizer (eg. Palatinol AH (a registered tradename)) and 2 parts of stabilizer. To color the material, it is worked on a heated mixing mill at 140° C. for from 8 to 10 minutes.

Whitened blends are obtainable analogously, eg. by additionally mixing 2.5 parts of TiO₂ (eg. grade RN 56) with 0.25 part of the dye obtained according to Example 1 and 50 parts of a plasticized PVC mixture.

EXAMPLE 3

In printing inks

5 Parts of the dye obtained according to Example 1, from 30 to 40 parts of a resin (eg. rosin modified with a phenol-formaldehyde resin) and from 65 to 55 parts of toluene are thoroughly mixed in a dispersing device. This gives a toluene-based gravure printing ink of excellent fastness to light and outstanding brilliance.

We claim:

1. A compound of the formula

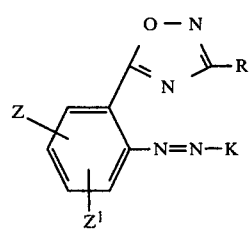

in which

K is

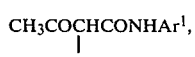

CH₃COCHCONHAr¹,

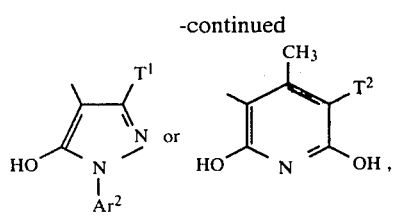 or 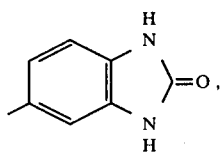

Ar¹ is phenyl; phenyl substituted by chlorine, methoxy, ethoxy, methyl, acetylamino or benzoylamino; or

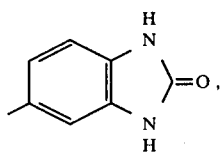

Ar² is phenyl; or phenyl substituted by chlorine, methyl or sulfamoyl,
T¹ is methyl or carbamoyl,
T² is cyano or carbamoyl,
Z is hydrogen, chlorine, bromine or trifluoromethyl,
Z¹ is hydrogen, chlorine, or bromine, and
R is phenyl; phenyl substituted by chlorine, bromine, hydroxy, methoxy, ethoxy, $C_1$ to $C_4$ alkyl, cyano, carbamoyl, nitro, phenyl, sulfamoyl, N-phenylsulfamoyl, acetylamino or benzoylamino; naphthyl; N-phenylphthalimidyl; or pyridyl.

2. A compound as set forth in claim 1 in which
Ar² is phenyl or phenyl substituted by chlorine or methyl,
T¹ is methyl
R is phenyl, phenyl substituted by chlorine, bromine, methyl, nitro or N-phenylphthalimidyl, and
K, Ar¹, T², Z and Z₁ have the meanings set forth in claim 1.

3. A compound as set forth in claim 1 of the formula:

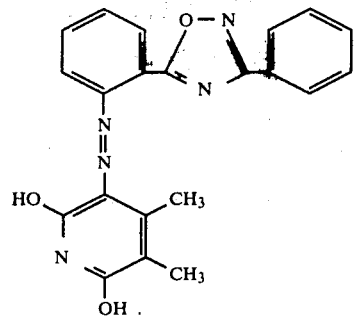

4. A compound as set forth in claim 1 of the formula:

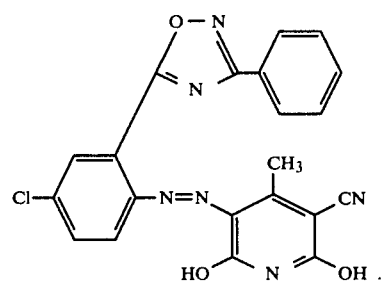

5. A compound as set forth in claim 1 of the formula:

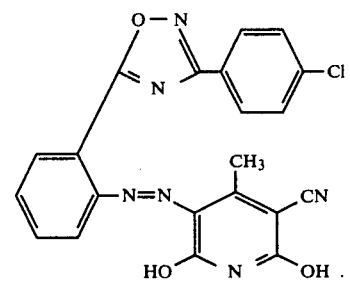

* * * * *

UNITED STATES PATENT AND TRADEMARK OFFICE
CERTIFICATE OF CORRECTION

PATENT NO. : 4,229,343
DATED : October 21, 1980
INVENTOR(S) : H. Junge, W. Kurtz, P. Dimroth & H. Scherer It is certified that error appears in the above-identified patent and that said Letters Patent are hereby corrected as shown below:

On Column 100, Claim 3, in the structural formula:

" 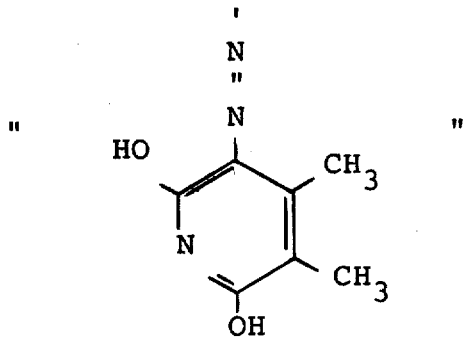 " should be 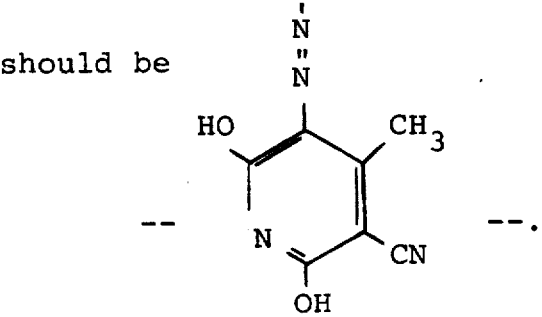 --.

Signed and Sealed this

Twenty-fourth Day of March 1981

[SEAL]

Attest:

RENE D. TEGTMEYER

Attesting Officer       Acting Commissioner of Patents and Trademarks